United States Patent
Itescu et al.

(10) Patent No.: US 9,480,713 B2
(45) Date of Patent: *Nov. 1, 2016

(54) METHOD FOR TREATING DIABETIC RENAL FAILURE OR SYNDROME X

(71) Applicant: Mesoblast, Inc., New York, NY (US)

(72) Inventors: Silviu Itescu, Melbourne (AU); Ravi Krishnan, Royston Park (AU)

(73) Assignee: MESOBLAST, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/535,827

(22) Filed: Nov. 7, 2014

(65) Prior Publication Data

US 2015/0064148 A1 Mar. 5, 2015

Related U.S. Application Data

(63) Continuation of application No. 13/129,180, filed as application No. PCT/AU2009/001511 on Nov. 19, 2009, now Pat. No. 8,894,972.

(60) Provisional application No. 61/199,796, filed on Nov. 20, 2008.

(51) Int. Cl.
  *A61K 35/12* (2015.01)
  *C12N 5/071* (2010.01)
  *A61K 45/06* (2006.01)

(52) U.S. Cl.
  CPC ............... *A61K 35/12* (2013.01); *A61K 45/06* (2013.01); *C12N 5/0676* (2013.01)

(58) Field of Classification Search
  CPC ..................................................... A61K 35/12
  See application file for complete search history.

(56) References Cited

PUBLICATIONS

Jun. 30, 2015 Office Action issued in connection with Japanese Patent Application No. 2011-536703.
Al-Quobaili and Montenarit, "Pancreatic duodenal homeobox factor-1 and diabetes mellitus type 2 (Review)," Int'l J. Mol. Med. 2008 (21) :399-404.
Liu and Han, "Mesenchymal stem cells: biology and clinical potential in type 1 diabetes therapy," J. Cell Mol. Med. 2008 (12) (4) :1155-68.
Bensidhoum et al., "Homing of in vitro Stro-1- or Stro-1+ human mesenchymal stem cells into the NOD/SCID mouse and their role in supporting human CD34 cell engraftment," Blood 2004(103) (9) :3313-19.
Chen et al., "Bioreactor Expansion of Human Adult Bone Marrow-Derived Mesenchymal Stem Cells," Stem Cells 2006(24) :2052-59.

*Primary Examiner* — Bin Shen
(74) *Attorney, Agent, or Firm* — John P. White; Cooper & Dunham LLP

(57) ABSTRACT

The present invention provides a method for improving pancreatic function in a subject in need thereof, the method comprising administering to the subject STRO-1$^+$ cells and/or progeny cells thereof and/or soluble factors derived therefrom. The method of the invention is useful for treating and/or preventing and/or delaying the onset or progression of a disorder resulting from or associated with pancreatic dysfunction, e.g., resulting from abnormal endocrine or exocrine function of the pancreas.

8 Claims, 16 Drawing Sheets

CONTROL  VEHICLE  STRO-1

METHOD FOR TREATING DIABETIC RENAL FAILURE OR SYNDROME X

This application is a continuation of U.S. Ser. No. 13/129,180, filed Jun. 22, 2011, now U.S. Pat. No. 8,894,972, issued Nov. 25, 2014, which is a §371 national stage of PCT International Application No. PCT/AU2009/001511, filed Nov. 19, 2009, which claims the benefit of U.S. Provisional Application No. 61/199,796, filed Nov. 20, 2008, the entire contents of each of which are hereby incorporated by reference into the subject application.

FIELD OF THE INVENTION

The present invention relates to a method for improving pancreatic function in a subject in need thereof. The method may be used for treating and/or preventing and/or delaying the onset or progression of a disorder resulting from or associated with pancreatic dysfunction, e.g., resulting from abnormal endocrine or exocrine function of the pancreas.

BACKGROUND OF THE INVENTION

The pancreas is a multifunctional gland organ in the digestive and endocrine system of vertebrates. It is both an endocrine gland (producing several hormones including insulin, glucagon, and somatostatin), and an exocrine gland (secreting pancreatic juice containing digestive enzymes that pass to the small intestine). The enzymes in the pancreatic juice help in the further breakdown of the carbohydrates, protein, and fat in the chyme.

The part of the pancreas with endocrine function is made up of numerous cell clusters called islets of Langerhans. There are four main cell types in the islets classified by their secretion: $\alpha$ cells secrete glucagon, $\beta$ cells secrete insulin, $\delta$ cells secrete somatostatin, and PP cells secrete pancreatic polypeptide. The islets are a compact collection of endocrine cells arranged in clusters and cords and also contain a network of capillaries. The capillaries of the islets are lined by layers of endocrine cells in direct contact with vessels, and most endocrine cells are in direct contact with blood vessels, by either cytoplasmic processes or by direct apposition.

In contrast to the endocrine pancreas, which secretes hormones into the blood, the exocrine pancreas produces digestive enzymes (e.g., trypsinogen, chymotrypsinogen, elastase, carboxypeptidase, pancreatic lipase, and amylase) and an alkaline fluid, and secretes these into the small intestine through a system of exocrine ducts in response to the small intestine hormones secretin and cholecystokinin. Digestive enzymes are produced and secreted by acinar cells of the exocrine pancreas. Specific cells that line the pancreatic ducts, called centroacinar cells, secrete a bicarbonate- and salt-rich solution into the small intestine.

Pancreatic dysfunction can lead to overproduction or underproduction of hormones and/or enzymes produced by the pancreas. Conditions associated with or caused by pancreatic dysfunction include diabetes mellitus, acute or chronic pancreatitis, pancreatic enzyme deficiency or pancreatic tumor.

Diabetes Mellitus (DM) is one of the most common chronic endocrine disorders across all age groups and populations, and is caused by pancreatic dysfunction. DM afflicts over 100 million people worldwide. In the United States alone, there are more than 12 million subjects diagnosed with DM, with 600,000 new cases diagnosed each year.

DM is a diagnostic term for a group of disorders characterized by abnormal carbohydrate (e.g., glucose) homeostasis or metabolism resulting in elevated blood sugar. These disorders comprise several interrelated metabolic, vascular, and neuropathic components. Various components of DM are caused by endocrine and/or exocrine functions of the pancreas. For example, the metabolic component, generally characterized by hyperglycemia, comprises alterations in carbohydrate, fat and protein metabolism caused by absent or markedly reduced secretion of hormones, particularly insulin (i.e., endocrine function) and/or ineffective insulin action. At an exocrine level, the pancreas produces various enzymes that are involved in digestion of food. For example, the pancreas produces amylase and in DM may secrete insufficient levels of this enzyme to digest carbohydrate leading to exocrine pancreatic insufficiency, malnutrition and weight loss. Accordingly, both the endocrine and exocrine functions of the pancreas contribute to the metabolic components of DM. The vascular component of DM comprises abnormalities in the blood vessels leading to cardiovascular, retinal and renal complications. Abnormalities in the peripheral and autonomic nervous systems are also components of DM.

DM is generally caused by a reduction in the amount or circulating insulin and/or a reduction in the responsiveness of cells in a subject to insulin. Insulin is essential in the metabolism of carbohydrates, fat, and protein. Insulin reduces blood glucose levels by allowing glucose to enter muscle cells and fat cells and by stimulating the conversion of glucose to glycogen (glycogenesis) as a carbohydrate store. Insulin also inhibits the release of stored glucose from liver glycogen (glycogenolysis) and slows the breakdown of fat to triglycerides, free fatty acids, and ketones. Additionally, insulin slows the breakdown of protein for glucose production (gluconeogenesis). Insulin is produced and secreted by $\beta$ cells in the islets of Langerhans of the pancreas.

There are several types of diabetes, including Type I (also referred to as insulin-dependent diabetes mellitus or IDDM) and Type II (also referred to as non-insulin-dependent diabetes mellitus or NIDDM), gestational diabetes and pre-diabetes (or impaired glucose metabolism). Of these, the two most common forms of diabetes are Type I and Type II diabetes. Type I diabetes (or insulin-dependent diabetes mellitus; IDDM) is caused by the absence, destruction, or loss of pancreatic $\beta$-cells resulting in an absolute deficiency of insulin. Type II diabetes (non-insulin dependent diabetes; NIDDM) is a heterogeneous disorder that is characterized by insulin resistance.

Type I Diabetes

The overall incidence of type I diabetes is approximately 15 cases per 100,000 individuals in the US alone. Approximately, 5 to 15 percent of all cases of diabetes are type I diabetes cases in the US, with physicians diagnosing about 10,000 new cases every year. Internationally, the incidence of type I diabetes varies from about 0.61 cases per 100,000 individuals in China to about 34.5 cases per 100,000 in Sardinia, and more than 40 cases per 100,000 in Finland. Many countries also report that the incidence rate of type I diabetes has doubled over the last 20 years.

The acute clinical onset of type I diabetes is characterized by symptoms, such as hyperglycemia, polyuria, polydipsia, weight loss, or blurred vision, alone or in combination, followed days or weeks later by ketoacidosis. Generally, the acute onset of the disease is considered to be preceded by a long, asymptomatic preclinical period, during which the insulin-secreting β-cells are progressively destroyed by the subject's immune system.

In healthy individuals, the pancreas normally contains 1 to 1.5 million islets; and approximately 80 percent of islet cells are insulin-producing β-cells. The symptoms of clinical diabetes appear when fewer than 10 percent of those β-cells remain.

The mismatch between insulin supply and demand caused by the loss of pancreatic β-cells leads to abnormal glucose, lipid and protein metabolism. Insulin deficiency may lead to hyperglycemia and hyperglycemic dehydration, elevated levels of free fatty acids, elevated serum ketone levels, increased levels of triglycerides, increased levels of very low density lipoproteins (VLDLs), increased levels of branched chain amino acids, a decrease in protein synthesis, and ketoacidosis. A subject with type I diabetes is likely to suffer from any one or more of a variety of vascular and neurologic complications. For example, type I diabetes patients are two times more likely than non-diabetics to have a heart attack; they are five times more likely to suffer from gangrene; seventeen times more likely to have complete renal failure, and twenty-five times more likely to lose their eyesight.

Treatment/Prophylaxis of Type 1 Diabetes

Currently, type I diabetes is treated by administration of exogenous insulin, exercise and dietary management. These forms of therapy do not correct the damage to the pancreas (i.e., replace the destroyed β-islet cells), but rather replace growth factors produced by the β-islet cells or attempt to avoid the requirement for these factors.

Most subjects suffering from type I diabetes require some form of insulin therapy. At this time, such therapy generally requires the subject monitoring blood glucose and/or insulin levels and injecting recombinant or purified insulin when required. New forms of insulin are also being developed to enable nasal or oral administration. However, this form of therapy requires continual monitoring by the subject and insulin administration at least once a day for the life of the subject. Should the subject neglect to administer insulin or administer too much insulin there is a risk of the development of, for example, hyperglycemia, hypoglycemia or ketoacidosis.

Additional compounds currently used for the treatment of type I diabetes include for example, sulfonylurea, biguanide, α-glucosidase inhibitor or thiazolidinedione. However, each of these compounds also suffers from significant disadvantages. For example, sulfonylurea causes hypoglycemia and hyperinsulinemia; biguanide causes lactic acidosis; α-glucosidase inhibitor causes gastro-intestinal side-effects; and thiazolidinedione has a long-onset of action, is associated with weight gain and requires frequent liver function testing.

Glucagon-like peptide-1 (GLP-1) has also been identified as a possible therapeutic for diabetes. This peptide induces expression of pancreatic and duodenal homeobox factor-1 (PDX-1), a transcription factor that plays a significant role in pancreas development, beta cell differentiation and maintenance of beta-cell function (Babu et al., *Mol Endocrinol.* 20:3133-3145, 2006). PDX-1 is involved in inducing the expression of glucose sensing and metabolism, such as GLUT2, glucokinase and insulin. GLP-1 has been suggested as a potential therapeutic because it may induce pancreatic beta cell expansion in a subject, in addition to stimulating insulin expression (Buteau, *Diabetes and Metabolism,* 34: S73-S77, 2008). However, use of clinically available agents that increase intracellular availability of GLP-1, such as orally active dipeptidyl peptidase-4 (DPPIV) inhibitors or injectable GLP-1 analogs, has been limited to the treatment of mild forms of type II diabetes. The relatively short half-life of these agents, their need for frequent administration, and their relative lack of potency in cases of severe beta cell loss have precluded their use as insulin-sparing agents for type 1 diabetes or other insulin-dependent patients. Even orally available GLP-1 analogs have short half life and require high-dose daily administration.

Other therapeutic options include pancreatic islet of Langerhans transplantation, which has been shown to reduce insulin dependency (Shapiro et al., *New Eng. J. Med.,* 343: 230-238, 2000). However, the application of this treatment is restricted by the very limited availability of primary human islets from donors, which must have a beating heart to ensure cell survival during transplantation (Burns et al., *J. Endocrinology,* 103: 437-443, 2004).

Stem cells, e.g., embryonic stem (ES) cells have also been proposed as a suitable source for the production of therapeutically relevant amounts of insulin-producing cells. However, insulin secreting β-cells have not been produced from stem cells, let alone at the level required, estimated at $2-4 \times 10^9$ β-cells per transplantation. Such cell-based therapies must also overcome such difficulties as the proliferative capacity of the replacement cells must be tightly controlled to ensure that they do not expand to a point that they cause hyperinsulinemia or hypoglycaemia, and the transplanted cells must avoid destruction by a recipient's immune system. Moreover, in the case of ES cell-based therapies, any remaining ES cells must be removed to avoid the risk of teratoma formation.

Type II Diabetes

Type II diabetes accounts for approximately 90-95% of diabetes cases and kills about 193,000 people per annum in USA alone. Type II diabetes is the seventh leading cause of all deaths. In Western societies, Type II diabetes currently affects 6% of the adult population with world-wide frequency expected to grow by 6% per annum. Notwithstanding that there are certain inheritable traits that may predispose particular individuals to developing Type II diabetes, the major cause of the current increase in incidence of the disease is the increased sedentary life-style, diet and obesity now prevalent in developed countries. Type II diabetes is now internationally recognized as one of the major threats to human health.

Type II diabetes, develops when muscle, fat and liver cells fail to respond normally to insulin. This failure to respond (called insulin resistance) may be due to reduced numbers of insulin receptors on these cells, or a dysfunction of signaling pathways within the cells, or both. The β-cells initially compensate for this insulin resistance by increasing their insulin output. Over time, these cells become unable to produce sufficient insulin to maintain normal glucose levels, indicating progression to Type II diabetes (Kahn et al, *Am. J. Med.* 108: 2S-8S), 2000)

Treatment of Type II Diabetes

Conventional treatments for Type II diabetes are very limited, and focus on attempting to control blood glucose levels to minimize or delay complications. Current treatments target either insulin resistance (metformin, thiazolidinediones ("TZDs")), or insulin release from the β-cells (sulphonylureas, exanatide). Sulphonylureas, and other compounds that act by depolarizing the beta cell, have the side effect of hypoglycemia since they cause insulin secretion independent of circulating glucose levels. Other side effects of current therapies include weight gain, loss in responsiveness to therapy over time, gastrointestinal problems, and edema.

One currently approved drug, Januvia (sitagliptin) increases blood levels of incretin hormones, which can increase insulin secretion, reduce glucagon secretion and have other less well characterized effects. However, Januvia and other dipeptidyl peptidase IV inhibitors may also influence the tissue levels of other hormones and peptides, and the long-term consequences of this broader effect have not been fully investigated. Moreover, this compound does not address problems associated with insulin resistance.

As with type I diabetes, GLP-1 has been suggested as a potential therapeutic for type II diabetes as a result of its ability to induce insulin secretion, induce beta cell expansion and restore glucose tolerance in glucose-resistant beta cells. However, as discussed above, GLP-1 and analogs thereof are very limited in their therapeutic potential as a result of their very short half life.

It is clear from the foregoing that there is a need in the art for a method to treat or prevent or delay the onset or progression of disorders associated with pancreatic function and/or for improving pancreatic function.

SUMMARY OF INVENTION

In work leading up to the present invention the inventors sought to determine the effect of a specific subset of mesenchymal precursor cells (MPCs) on the development and/or progression of pancreatic dysfunction. The inventors made use of a recognized model in which pancreatic dysfunction is induced by administering streptozotocin (STZ) to a mouse. This compound induces inflammation and immune cell infiltration of the pancreatic islets ultimately resulting in cell death and pancreatic dysfunction. STZ causes dysfunction in both the endocrine functions of the pancreas (e.g., reducing insulin production) and the exocrine functions of the pancreas (e.g., reducing amylase production). This model is also an accepted model of a glucose metabolism disorder, e.g., Type I diabetes or Type II diabetes.

As exemplified herein, the inventors have demonstrated that administration of STRO-1$^+$ cells to STZ treated mice increases serum insulin levels and reduces blood glucose levels compared to STZ treated mice that have not received STRO-1$^+$ cells. The inventors also demonstrated that STRO-1$^+$ cells induced or increase the number of PDX-1 expressing cells in the pancreas and/or increase the number of pancreatic beta cells and/or islets in a subject (e.g., promote pancreatic beta cell regeneration). The inventors also found that STRO-1$^+$ cells restore the ratio of pancreatic beta cells to pancreatic alpha cells by increasing beta cell numbers and/or reducing alpha cell numbers. The inventors additionally found that treatment with STRO-1$^+$ cells induces blood vessel formation in the pancreas of a subject. Together these data indicate that STRO-1$^+$ cells and/or progeny cells thereof and/or factors secreted therefrom induce or promote pancreatic regeneration and/or improve pancreatic function. Accordingly, the STRO-1$^+$ cells or progeny cell thereof or a factor derived therefrom are capable or treating and/or preventing and/or reducing the toxic effects of STZ of the pancreas. It follows that these data indicate that the STRO-1$^+$ cells or progeny cells thereof or one or more factors derived therefrom are capable of treating or preventing or delaying the onset of or reducing the severity of pancreatic dysfunction and/or improving pancreatic function and/or inducing regeneration of pancreas or cells thereof and/or improving glucose metabolism (e.g., by increasing circulating insulin levels).

The inventors' findings provide the basis for methods for treating and/or preventing and/or delaying the onset of and/or delaying the progression of pancreatic dysfunction, such as diabetes.

Accordingly, the present invention provides a method for improving pancreatic function in a subject in need thereof, the method comprising administering to the subject STRO-1$^+$ cells and/or progeny cells thereof and/or soluble factors derived therefrom.

The present invention additionally or alternatively provides a method for promoting or inducing pancreatic regeneration in a subject (e.g., in a subject suffering from pancreatic dysfunction), said method comprising administering to the subject STRO-1$^+$ cells and/or progeny cells thereof and/or soluble factors derived therefrom. For example, the method induces or promotes production of new beta cells and/or microvessels in a pancreas.

The present invention additionally or alternatively provides a method for inducing or promoting regeneration of pancreatic beta cells and/or pancreatic islets, the method comprising administering to the subject STRO-1$^+$ cells and/or progeny cells thereof and/or soluble factors derived therefrom.

The present invention additionally or alternatively provides a method for reducing blood glucose levels and/or increasing blood/serum insulin levels in a subject, the method comprising administering to the subject STRO-1$^+$ cells and/or progeny cells thereof and/or soluble factors derived therefrom.

The present invention additionally or alternatively provides a method for increasing the number of pancreatic beta cells and/or for increasing the number of pancreatic beta cells relative to pancreatic alpha cells and/or for reducing the number of pancreatic alpha cells and/or for increasing the number of pancreatic islets in a subject, the method comprising administering to the subject STRO-1$^+$ cells and/or progeny cells thereof and/or soluble factors derived therefrom.

The present invention additionally or alternatively provides a method for increasing pancreatic and duodenal homeobox factor-1 (PDX-1) expression and/or for increasing the number of PDX-1 expressing cells in a pancreas of a subject, the method comprising administering to the subject STRO-1$^+$ cells and/or progeny cells thereof and/or soluble factors derived therefrom.

The present invention additionally or alternatively provides a method for inducing or promoting arterio genesis or angiogenesis in the pancreas of a subject, the method comprising administering to the subject STRO-1$^+$ cells and/or progeny cells thereof and/or soluble factors derived therefrom.

The present invention additionally or alternatively provides a method for increasing the number of pancreatic beta cell precursors or inducing or promoting proliferation of pancreatic beta cell precursors in a subject, the method comprising administering to the subject STRO-1$^+$ cells and/or progeny cells thereof and/or soluble factors derived therefrom.

In one example, a subject suffers from pancreatic dysfunction.

In one example, the pancreatic dysfunction is associated with or results from dysfunction of the endocrine function of the pancreas and/or the exocrine function of the pancreas. Preferably, the pancreatic dysfunction results in or is associated with reduced pancreatic function, e.g., reduced pancreatic endocrine function or reduced pancreatic exocrine function.

In one example of the present invention, pancreatic dysfunction is associated with or causes a carbohydrate metabolism disorder. Such a carbohydrate metabolism disorder can be cause by pancreatic endocrine and/or exocrine dysfunction. In one example, the carbohydrate metabolism disorder is caused by reduced insulin production by the pancreas. In another example, the carbohydrate metabolism disorder is caused by increased glucagon levels (e.g., increased numbers of alpha cells and/or increased glucagon expression and/or production and/or secretion). In another example, the carbohydrate metabolism disorder is caused by reduced amylase production by the pancreas. The skilled artisan will be aware based on the description herein that a carbohydrate metabolism disorder (or pancreatic dysfunction) need not be solely characterized by pancreatic function. For example, a carbohydrate metabolism disorder may also be characterized by insulin resistance and/or by a vascular component and/or by a neuropathic component. In one example of the present invention, the pancreatic dysfunction is diabetes mellitus, e.g., type I diabetes mellitus or type II diabetes mellitus.

Preferably, the method of the present invention comprises administering an effective amount or a therapeutically or prophylactically effective amount of STRO-1$^+$ cells and/or progeny cells thereof and/or soluble factors derived therefrom. In one example, the method comprises administering an amount of STRO-1$^+$ cells and/or progeny cells thereof and/or soluble factors derived therefrom sufficient to induce insulin production in a subject, preferably to induce insulin production for at least about 1 week or 2 weeks or 3 weeks or 4 weeks.

In one example, the STRO-1$^+$ cells and/or progeny cells thereof and/or soluble factors derived therefrom are administered directly into the bloodstream of a subject, however other sites of administration are not excluded. Preferably, the STRO-1$^+$ cells and/or progeny cells thereof and/or soluble factors derived therefrom are administered systemically. For example, the STRO-1$^+$ cells and/or progeny cells thereof and/or soluble factors derived therefrom are administered intravenously, intra-arterially, into an aorta, into an atrium or ventricle of the heart or into a blood vessel connected to a pancreas, e.g., an abdominal aorta, a superior mesenteric artery, a pancreaticoduodenal artery or a splenic artery. In a preferred example, the STRO-1$^+$ cells and/or progeny cells thereof and/or soluble factors derived therefrom are administered intra-arterially, e.g., into a femoral artery or into a celiac artery, e.g., using a catheter.

Alternatively, or in addition, the STRO-1$^+$ cells and/or progeny cells thereof and/or soluble factors derived therefrom are administered to the pancreas or a part thereof of a subject.

In one example, the STRO-1$^+$ cells administered to the subject are STRO-1$^{bri}$, and/or express tissue non-specific alkaline phosphatase (TNAP). Additional populations of STRO-1$^+$ cells characterized by specific cell surface markers or combinations thereof are described herein. In accordance with this example, progeny cells and/or soluble factors may also be derived from cells expressing STRO-1 or that are STRO-1$^{bri}$ and/or expressing TNAP. Such progeny cells may also express STRO-1 or be STRO-1$^{bri}$ and/or express TNAP.

In accordance with examples of the invention directed to treating or delaying the progression of pancreatic dysfunction, it is preferred that the STRO-1$^+$ cells and/or progeny cells thereof and/or soluble factors derived therefrom are administered following diagnosis of the disorder, e.g., using standard methods known in the art. For those examples directed to preventing or delaying the onset of pancreatic dysfunction, it is preferred that the STRO-1$^+$ cells and/or progeny cells thereof and/or soluble factors derived therefrom are administered prior to clinical diagnosis of the disorder, e.g., when the subject suffers from impaired glucose tolerance and/or impaired fasting glycemia and/or in the case of Type I diabetes prior to or concomitant with an autoimmune response such as indicated by expansion of a population of T cells and/or B cells and/or by the production of autoantibodies (e.g., expansion of cytotoxic T cells against pancreatic β-islet cells and/or autoantibodies against one or more pancreatic β-islet cell markers in the onset or progression of type 1 diabetes).

Preferably, a method as described herein according to any example additionally comprises monitoring or detecting onset and/or progression of pancreatic dysfunction and/or blood glucose levels and/or blood/serum insulin levels and/or the number of beta cells and/or the number of alpha cells and/or the number of pancreatic islets and/or the number of PDX-1 expressing cells and/or the amount of PDX-1 expression and/or the number of blood vessels. For example, the method additionally comprises glucose tolerance testing and/or by fasting glycemia testing and/or by measuring levels of a hormone or enzyme produced by the pancreas and/or obtaining a sample of a pancreas to determine the number of beta cells and/or the number of alpha cells and/or the number of pancreatic islets and/or the number of PDX-1 expressing cells and/or the amount of PDX-1 expression and/or the number of blood vessels. Such monitoring may indicate that a subsequent administration of STRO-1$^+$ cells and/or progeny cells thereof and/or soluble factors derived therefrom is required or desirable.

As will be apparent to the skilled artisan from the preceding paragraph, a method as described herein according to any example shall not be considered to be limited to a single administration of STRO-1$^+$ cells and/or progeny cells thereof and/or soluble factors derived therefrom. The present invention explicitly encompasses multiple administrations either to the same or different sites or through the same or different routes. The present invention also contemplates a single administration of STRO-1$^+$ cells and/or progeny cells thereof and/or soluble factors derived therefrom.

In one example, the STRO-1$^+$ cells and/or progeny cells thereof and/or soluble factors derived therefrom are administered in the form of a composition, e.g., a composition comprising said STRO-1$^+$ cells and/or progeny cells thereof and/or soluble factors derived therefrom and a carrier and/or excipient. Suitable carriers and/or excipients will be apparent to the skilled artisan and/or described herein.

Such a composition may comprise additional factors useful for treating or preventing a carbohydrate metabolism disorder, e.g., insulin or amylase and/or a peptide or polypeptide associated with normal pancreatic function e.g., cholycystokinin octapeptide or somatostatin or glucagon or trypsinogen or chymotrypsinogen or elastase or carboxypeptidase or pancreatic lipase. Alternatively, or in addition, a STRO-1$^+$ cell or progeny cell thereof may be genetically-modified to express and, preferably secrete, such an additional factor, e.g., insulin or amylase and/or a peptide or polypeptide associated with normal pancreatic function e.g., cholycystokinin octapeptide or somatostatin or glucagon or trypsinogen or chymotrypsinogen or elastase or carboxypeptidase or pancreatic lipase.

The present invention also provides for use of STRO-1$^+$ cells and/or progeny cells thereof and/or soluble factors derived therefrom or a composition comprising same for:
(i) treatment of pancreatic dysfunction; and/or
(ii) improving pancreatic function; and/or (iii) inducing or promoting regeneration of pancreatic beta cells and/or pancreatic islets; and/or
(iv) reducing blood glucose levels and/or increasing blood/serum insulin levels; and/or
(v) increasing the number of pancreatic beta cells and/or for increasing the number of pancreatic beta cells relative to pancreatic alpha cells and/or for reducing the number of pancreatic alpha cells and/or for increasing the number of pancreatic islets; and/or
(vi) increasing pancreatic and duodenal homeobox factor-1 (PDX-1) expression and/or for increasing the number of PDX-1 expressing cells in a pancreas; and/or
(vii) inducing or promoting arteriogenesis or angiogenesis in the pancreas.

The present invention also provides for use of STRO-1$^+$ cells and/or progeny cells thereof and/or soluble factors derived therefrom in the manufacture of a medicament for:
(i) treatment of pancreatic dysfunction; and/or
(ii) improving pancreatic function; and/or
(iii) inducing or promoting regeneration of pancreatic beta cells and/or pancreatic islets; and/or
(iv) reducing blood glucose levels and/or increasing blood/serum insulin levels; and/or
(v) increasing the number of pancreatic beta cells and/or for increasing the number of pancreatic beta cells relative to pancreatic alpha cells and/or for reducing the number of pancreatic alpha cells and/or for increasing the number of pancreatic islets; and/or
(vi) increasing pancreatic and duodenal homeobox factor-1 (PDX-1) expression and/or for increasing the number of PDX-1 expressing cells in a pancreas; and/or
(vii) inducing or promoting arteriogenesis or angiogenesis in the pancreas.

The present invention is applicable to a wide range of animals. For example, the subject is a mammal such as a human, dog, cat, horse, cow, or sheep, preferably, the subject is a human. In one example the subject is a human. In another example, the subject is a non-human mammal.

DETAILED DESCRIPTION OF THE PREFERRED EMBODIMENTS

General Techniques and Selected Definitions

Figure 1:
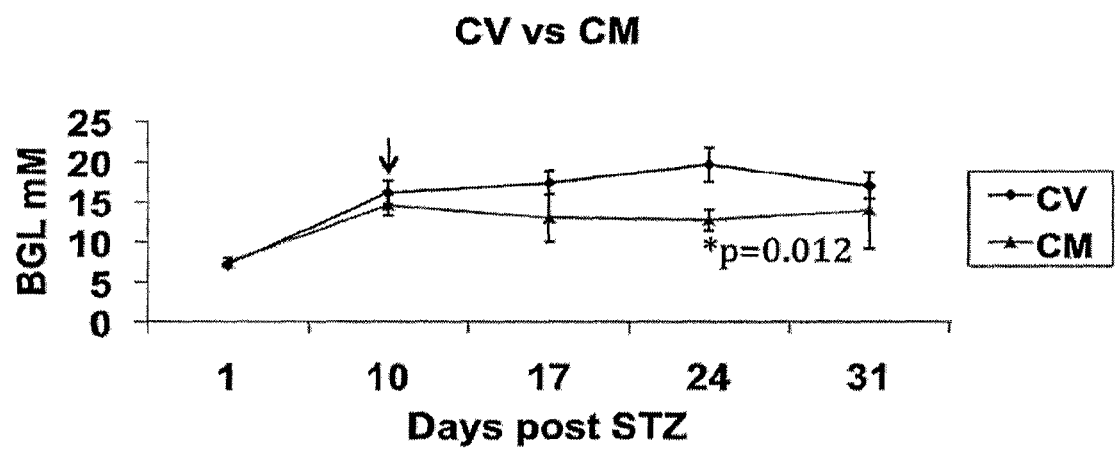
FIG. 1 is a graphical representation depicting the effects of STRO-1$^+$ cells on blood glucose levels (BGL) in STZ-induced diabetic NOD/scid mice. Blood glucose levels were determined in diabetic mice who were injected at day 10 post-STZ therapy (arrows) with STRO-1+ cells in the left ventricle (CM) or with vehicle (CV). Blood glucose values are mean glucose (mM)+/−SE. Student's t-test was performed with significance at $p<0.05$.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment or example described herein is to be applied mutatis mutandis to each and every other embodiment unless specifically stated otherwise. For example, each embodiment or example described herein directed to treating and/or preventing and/or delaying the onset of and/or delaying the progression of pancreatic dysfunction in a subject is to be applied mutatis mutandis to methods for improving pancreatic function and/or for inducing or promoting pancreatic regeneration as if those embodiments were explicitly recited herein.

Each embodiment described herein in respect of treatment of pancreatic dysfunction shall be taken to apply mutatis mutandis to the treatment of a carbohydrate metabolism disorder as if those embodiments were explicitly recited herein.

Each embodiment described herein in respect of treatment of pancreatic dysfunction shall be taken to apply mutatis mutandis to the treatment of diabetes mellitus, e.g., type I diabetes mellitus or type II diabetes mellitus as if those embodiments were explicitly recited herein.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and DI; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, ppl-22; Atkinson et al, pp 35-81; Sproat et al, pp 83-115; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (Interactiva, Germany); Sakakibara, D., Teichman, J., Lien, E. Land Fenichel, R. L. (1976). *Biochem. Biophys. Res. Commun.* 73 336-342; Merrifield, R. B. (1963). *J. Am. Chem. Soc.* 85, 2149-2154; Barany, G. and Merrifield, R. B. (1979) in The Peptides (Gross, E. and Meienhofer, J. eds.), vol. 2, pp. 1-284, Academic Press, New York. 12. Wünsch, E., ed. (1974) Synthese von Peptiden in Houben-Weyls Metoden der Organischen Chemie (Müler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) *Int. J. Peptide Protein Res.* 25, 449-474; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000), ISBN 0199637970, whole of text.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

As used herein the term "derived from" shall be taken to indicate that a specified integer may be obtained from a particular source albeit not necessarily directly from that source. In the context of soluble factors derived from STRO-1⁺ cells and/or progeny cells thereof, this term shall be taken to mean one or more factors, e.g., proteins, peptides, carbohydrates, etc, produced during in vitro culturing of STRO-1⁺ cells and/or progeny cells thereof.

As used herein, the term "improving pancreatic function" shall be taken to mean one or more functions of a pancreas in a subject is enhanced compared to that same function in a subject that has not been treated according to the present invention (preferably, in the subject prior to treatment). Such a term encompasses, e.g., increasing the level of insulin secretion or improving regulation of insulin secretion in a subject that may or may not be suffering from a glucose metabolism disorder. The term also encompasses reducing secretion of, e.g., glucagon in a subject having increased levels of that hormone (e.g., as a result of a glucagon secreting tumor) and/or a subject that suffers from hypoglycemia.

As used herein, the term "pancreatic dysfunction" shall be taken to mean any condition in which one or more of the functions of a pancreas in a subject is/are different to the same function in a normal and/or healthy individual. For example, the term "pancreatic dysfunction" encompasses conditions in which an endocrine function and/or an exocrine function of a pancreas in a subject is/are enhanced or reduced compared to a normal and/or healthy individual. For example, "pancreatic dysfunction" may be characterized by, associated with or caused by aberrant (i.e., increased or reduced) levels of insulin, glucagon, somatostatin, pancreatic polypeptide, trypsinogen, chymotrypsinogen, elastase, carboxypeptidase, pancreatic lipase or amylase. It will be apparent to the skilled artisan from the foregoing that the term "treating pancreatic dysfunction" encompasses normalizing a function of the pancreas (e.g., treating a subject such that one or more functions of the pancreas that are abnormal are reduced or enhanced such that they are more similar to the same function in a normal and/or healthy individual). For example, such treatment may result in increased insulin levels and/or increased numbers of pancreatic beta cells and/or pancreatic islets in a subject having aberrantly reduced levels of insulin and/or beta cells and/or islets. Such treatment may equally reduce aberrantly increased glucagon levels, e.g., in the case of a glucagon secreting tumor of the pancreas, e.g., by reducing the number of glucagon secreting alpha cells and/or by reducing glucagon expression, production and/or secretion. The meaning of the term "preventing or delaying pancreatic dysfunction" will be apparent to the skilled artisan based on the foregoing.

Pancreatic dysfunction may be associated with or cause a condition resulting in malabsorption of nutrients, e.g., carbohydrate, lipid or protein, e.g., as a result of a reduced level of a digestive enzyme produced by the pancreas, e.g., lipase or amylase and/or by reduced production of pancreatic juice. Such conditions include pancreatitis, pancreatic insufficiency, acquired autoimmune deficiency syndrome, cancer, cystic fibrosis or Zollinger Ellison syndrome. In a preferred example, the condition is caused by or associated with reduced amylase or lipase produced by the pancreas.

Pancreatic dysfunction may also be associated with or causative of a condition associated with aberrant use or metabolism of nutrients by a subject, e.g., resulting in hyperglycemia or hypoglycemia, reduced serum amino acid levels, proteinuria, necrolytic migratory erythema. Such conditions include carbohydrate metabolism disorders, e.g., diabetes mellitus. Other conditions include, for example, tumors (e.g., glucagon secreting tumors, which can cause hyperglycemia). Exemplary tumors include glucagonomas.

As used herein, the term "carbohydrate metabolism disorder" shall be taken to mean any disorder in which a subject is unable to or has a reduced ability to break down or metabolize or to take up or use one or more forms of carbohydrate, generally leading to increased levels of that/those carbohydrate(s) in the blood stream of the subject. Preferably, the carbohydrate metabolism disorder is associated with or caused by reduced production by the pancreas of a hormone involved in breaking down a carbohydrate, e.g., production of amylase. More preferably, the carbohydrate metabolism disorder is associated with or caused by reduced production by the pancreas of a hormone involved in uptake of a carbohydrate, e.g., production of insulin. Exemplary carbohydrate metabolism disorders include Type I diabetes mellitus, Type II diabetes mellitus, idiopathic Type I diabetes (Type Ib), early-onset Type II diabetes (EOD), youth-onset atypical diabetes (YOAD), maturity onset diabetes of the young (MODY), malnutrition-related diabetes, gestational diabetes, conditions of impaired glucose tolerance (IGT), conditions of impaired fasting plasma glucose, metabolic acidosis, ketosis, syndrome X, hyperglycemia, hypoinsulinemia, insulin resistance, alpha mannosidosis, beta mannosidosis, fructose intolerance, fucosidosis, galactosemia, Leigh disease, mucolipidosis, mucopolysaccharidoses or a complication of any one or more of the preceding. Preferably, the carbohydrate metabolism disorder is diabetes, for example, Type I diabetes or Type II diabetes.

Preferably, a subject suffering from diabetes has a clinically accepted marker of diabetes, such as:

Fasting plasma glucose of greater than or equal to 7 nmol/L or 126 mg/dl;

Casual plasma glucose (taken at any time of the day) of greater than or equal to 11.1 nmol/L or 200 mg/dl with the symptoms of diabetes.

Oral glucose tolerance test (OGTT) value of greater than or equal to 11.1 nmol/L or 200 mg/dl measured at a two-hour interval. The OGTT is given over a two or three-hour time span.

As used herein, the term "effective amount" shall be taken to mean a sufficient quantity of STRO-1⁺ cells and/or progeny cells thereof and/or soluble factors derived therefrom to improve pancreatic function in a subject to which the STRO-1⁺ cells and/or progeny cells thereof and/or soluble factors derived therefrom are administered compared to their pancreatic function prior to administration and/or compared to a subject to which the STRO-1⁺ cells and/or progeny cells thereof and/or soluble factors derived therefrom are not administered. For example, an effective amount of STRO-1⁺ cells and/or progeny cells thereof and/or soluble factors derived therefrom may reduce basal or resting glucose levels (glycemia) and/or improve glucose tolerance and/or increase blood insulin levels and/or increase levels of glucagon, somatostatin, pancreatic polypeptide, trypsinogen, chymotrypsinogen, elastase, carboxypeptidase, pancreatic lipase or amylase in serum or in the pancreas or in the digestive system. An effective amount of STRO-1⁺ cells and/or progeny cells thereof and/or soluble factors derived therefrom may also increase blood supply to a pancreas or a region thereof, e.g., by increasing the vasculature around or within a pancreas or a region thereof. The skilled artisan will be aware that such an amount will vary depending on, for example, the STRO-1⁺ cells and/or progeny cells thereof and/or soluble factors derived therefrom and/or the particular subject and/or the type or severity of the pancreatic dysfunction. Accordingly, this term is not to be construed to limit the invention to a specific quantity, e.g., weight or number of cells or soluble factors, rather the present invention encompasses any amount of the STRO-1+ cells and/or progeny cells thereof and/or soluble factors derived therefrom sufficient to improve pancreatic function in a subject. Methods for detecting pancreatic function and/or for determining the amount of STRO-1+ cells and/or progeny cells thereof and/or soluble factors derived therefrom sufficient to improve pancreatic function will be apparent to the skilled artisan and/or described herein. An effective amount need not necessarily treat or prevent pancreatic dysfunction.

As used herein, the term "therapeutically effective amount" shall be taken to mean a sufficient quantity of STRO-1+ cells and/or progeny cells thereof and/or soluble factors derived therefrom to reduce or inhibit one or more symptoms of a clinical condition associated with or caused by pancreatic dysfunction to a level that is below that observed and accepted as clinically diagnostic of that condition. For example, a therapeutically effective amount of STRO-1+ cells and/or progeny cells thereof and/or soluble factors derived therefrom may reduce glucose tolerance in a subject from a level observed in a diabetic subject to a level observed in a presymptomatic subject (e.g., suffering from impaired glucose tolerance or impaired resting glycemia) or in a normal or healthy subject.

As used herein, the term "prophylactically effective amount" shall be taken to mean a sufficient quantity of STRO-1+ cells and/or progeny cells thereof and/or soluble factors derived therefrom to prevent or inhibit the onset of one or more detectable symptoms of a clinical condition associated with or caused by pancreatic dysfunction. For example, a prophylactically effective amount of STRO-1+ cells and/or progeny cells thereof and/or soluble factors derived therefrom may prevent glucose tolerance in a subject becoming impaired to such a degree that the subject is clinically diagnosed with diabetes.

As used herein, the term "treat" or "treatment" or "treating" shall be understood to mean administering a therapeutically effective amount of soluble factors and/or cells and reducing or inhibiting at least one symptom of a clinical condition associated with or caused by pancreatic dysfunction.

As used herein, the term "prevent" or "preventing" or "prevention" shall be taken to mean administering a prophylactically effective amount of soluble factors and/or cells and stopping or hindering the development of at least one symptom of a clinical condition associated with or caused by pancreatic dysfunction.

By "delaying progression of pancreatic dysfunction" is meant that a treatment reduces the severity of pancreatic dysfunction in a subject. Such a reduction in severity may be, for example, prevention of one or more complications of pancreatic dysfunction, such as, for example, nutrient malabsorption, hypoglycemia, hyperglycemia, ketoacidosis, retinopathy, cataracts, hypertension, renal failure, coronary artery disease, peripheral vascular disease, neuropathy (e.g., peripheral neuropathy or autonomic neuropathy) or increased risk of infection. Alternatively, or in addition, a reduction in severity of pancreatic dysfunction is characterized by a reduction in the requirement for therapeutic treatment (e.g., insulin administration) or the regularity of therapeutic treatment of a subject compared to a subject that has not received treatment using the method of the invention. Alternatively, or in addition, "reducing pancreatic dysfunction progression" is a delay in the onset of one or more detectable symptoms of pancreatic dysfunction compared to a diabetic subject that has not received treatment with a compound that reduces pancreatic dysfunction progression.

As used herein, the term "soluble factors" shall be taken to mean any molecule, e.g., protein, peptide, glycoprotein, glycopeptide, lipoprotein, lipopeptide, carbohydrate, etc. produced by STRO-1+ cells and/or progeny thereof that are water soluble. Such soluble factors may be intracellular and/or secreted by a cell. Such soluble factors may be a complex mixture (e.g., supernatant) and/or a fraction thereof and/or may be a purified factor. In one example of the present invention soluble factors are or are contained within supernatant. Accordingly, any example herein directed to administration of one or more soluble factors shall be taken to apply mutatis mutandis to the administration of supernatant.

As used herein, the term "supernatant" refers to the non-cellular material produced following the in vitro culturing of mesenchymal precursor cells, and/or progeny cells thereof, in a suitable medium, preferably liquid medium. Typically, the supernatant is produced by culturing the cells in the medium under suitable conditions and time, followed by removing the cellular material by a process such as centrifugation. The supernatant may or may not have been subjected to further purification steps before administration. In preferred example, the supernatant comprises less than $10^5$, more preferably less than $10^4$, more preferably less than $10^3$ and even more preferably no live cells.

As used herein, the term "normal or healthy individual" shall be taken to mean a subject that does not suffer from pancreatic dysfunction as assessed by any method known in the art and/or described herein.

STRO-1+ Cells or Progeny Cells, and Supernatant or One or More Soluble Factors Derived Therefrom STRO-1+ cells are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are capable of differentiating into germ lines such as mesoderm and/or endoderm and/or ectoderm.

In one embodiment, the STRO-1+ cells are multipotential cells which are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. STRO-1+ multipotential cells are thus non-hematopoietic progenitor cells which divide to yield daughter cells that are either stem cells or are precursor cells which in time will irreversibly differentiate to yield a phenotypic cell.

In a preferred example, the STRO-1+ cells are enriched from a sample obtained from a subject, e.g., a subject to be treated or a related subject or an unrelated subject (whether of the same species or different). The terms 'enriched', 'enrichment' or variations thereof are used herein to describe a population of cells in which the proportion of one particular cell type or the proportion of a number of particular cell types is increased when compared with the untreated population.

In a preferred example, the cells used in the present invention express one or more markers individually or collectively selected from the group consisting of TNAP+, VCAM-1+, THY-1+, STRO-2+, CD45+, CD146+, 3G5+ or any combination thereof.

By "individually" is meant that the invention encompasses the recited markers or groups of markers separately, and that, notwithstanding that individual markers or groups of markers may not be separately listed herein the accompanying claims may define such marker or groups of markers separately and divisibly from each other.

By "collectively" is meant that the invention encompasses any number or combination of the recited markers or groups of peptides, and that, notwithstanding that such numbers or combinations of markers or groups of markers may not be specifically listed herein the accompanying claims may define such combinations or sub-combinations separately and divisibly from any other combination of markers or groups of markers.

Preferably, the STRO-1$^+$ cells are STRO-1$^{bright}$ (syn. STRO-1$^{bri}$). Preferably, the STRO-1$^{bright}$ cells are additionally one or more of TNAP$^+$, VCAM-1$^+$, THY-1$^+$, STRO-2$^+$ and/or CD146$^+$.

In one example, the mesenchymal precursor cells are perivascular mesenchymal precursor cells as defined in WO 2004/85630.

A cell that is referred to as being "positive" for a given marker it may express either a low (lo or dim) or a high (bright, bri) level of that marker depending on the degree to which the marker is present on the cell surface, where the terms relate to intensity of fluorescence or other marker used in the sorting process of the cells. The distinction of lo (or dim or dull) and bri will be understood in the context of the marker used on a particular cell population being sorted. A cell that is referred to as being "negative" for a given marker is not necessarily completely absent from that cell. This terms means that the marker is expressed at a relatively very low level by that cell, and that it generates a very low signal when detectably labeled or is undetectable above background levels.

The term "bright", when used herein, refers to a marker on a cell surface that generates a relatively high signal when detectably labeled. Whilst not wishing to be limited by theory, it is proposed that "bright" cells express more of the target marker protein (for example the antigen recognized by STRO-1) than other cells in the sample. For instance, STRO-1$^{bri}$ cells produce a greater fluorescent signal, when labeled with a FITC-conjugated STRO-1 antibody as determined by fluorescence activated cell sorting (FACS) analysis, than non-bright cells (STRO-1$^{dull/dim}$). Preferably, "bright" cells constitute at least about 0.1% of the most brightly labeled bone marrow mononuclear cells contained in the starting sample. In other examples, "bright" cells constitute at least about 0.1%, at least about 0.5%, at least about 1%, at least about 1.5%, or at least about 2%, of the most brightly labeled bone marrow mononuclear cells contained in the starting sample. In a preferred example, STRO-1$^{bright}$ cells have 2 log magnitude higher expression of STRO-1 surface expression relative to "background", namely cells that are STRO-1$^-$. By comparison, STRO-1$^{dim}$ and/or STRO-1$^{intermediate}$ cells have less than 2 log magnitude higher expression of STRO-1 surface expression, typically about 1 log or less than "background".

As used herein the term "TNAP" is intended to encompass all isoforms of tissue non-specific alkaline phosphatase. For example, the term encompasses the liver isoform (LAP), the bone isoform (BAP) and the kidney isoform (KAP). In a preferred example, the TNAP is BAP. In a particularly preferred example, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in a preferred example, the STRO-1$^+$ cells are capable of giving rise to clonogenic CFU-F.

It is preferred that a significant proportion of the STRO-1$^+$ multipotential cells are capable of differentiation into at least two different germ lines. Non-limiting examples of the lineages to which the multipotential cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In another example, the STRO-1$^+$ cells are not capable of giving rise, upon culturing, to hematopoietic cells.

In one example, the cells are taken from the subject to be treated, cultured in vitro using standard techniques and used to obtain supernatant or soluble factors or expanded cells for administration to the subject as an autologous or allogeneic composition. In an alternative example, cells of one or more of the established human cell lines are used. In another useful example of the invention, cells of a non-human animal (or if the patient is not a human, from another species) are used.

The present invention also contemplates use of supernatant or soluble factors obtained or derived from STRO-1$^+$ cells and/or progeny cells thereof (the latter also being referred to as expanded cells) which are produced from in vitro culture. Expanded cells of the invention may a have a wide variety of phenotypes depending on the culture conditions (including the number and/or type of stimulatory factors in the culture medium), the number of passages and the like. In certain examples, the progeny cells are obtained after about 2, about 3, about 4, about 5, about 6, about 7, about 8, about 9, or about 10 passages from the parental population. However, the progeny cells may be obtained after any number of passages from the parental population.

The progeny cells may be obtained by culturing in any suitable medium. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells. In other words, a nutrient rich liquid prepared for bacterial culture is a medium. A powder mixture that when mixed with water or other liquid becomes suitable for cell culture may be termed a "powdered medium".

In an example, progeny cells useful for the methods of the invention are obtained by isolating TNAP$^+$ STRO-1$^+$ cells from bone marrow using magnetic beads labeled with the STRO-3 antibody, and then culture expanding the isolated cells (see Gronthos et al. *Blood* 85: 929-940, 1995 for an example of suitable culturing conditions).

In one example, such expanded cells (progeny) (preferably, at least after 5 passages) can be TNAP$^-$, CC9$^+$, HLA class I$^+$, HLA class II$^-$, CD14$^-$, CD19$^-$, CD3$^-$, CD11a$^-$c$^-$, CD31$^-$, CD86$^-$, CD34$^-$ and/or CD80$^-$. However, it is possible that under different culturing conditions to those described herein that the expression of different markers may vary. Also, whilst cells of these phenotypes may predominate in the expended cell population it does not mean that there is a minor proportion of the cells do not have this phenotype(s) (for example, a small percentage of the expanded cells may be CC9$^-$). In one preferred example, expanded cells still have the capacity to differentiate into different cell types.

In one example, an expended cell population used to obtain supernatant or soluble factors, or cells per se, comprises cells wherein at least 25%, more preferably at least 50%, of the cells are CC9+.

In another example, an expanded cell population used to obtain supernatant or soluble factors, or cells per se, comprises cells wherein at least 40%, more preferably at least 45%, of the cells are STRO-1$^+$.

In a further example, the expanded cells may express one or more markers collectively or individually selected from the group consisting of LFA-3, THY-1, VCAM-1, ICAM-1, PECAM-1, P-selectin, L-selectin, 3G5, CD49a/CD49b/CD29, CD49c/CD29, CD49d/CD29, CD 90, CD29, CD18, CD61, integrin beta 6-19, thrombomodulin, CD10, CD13, SCF, PDGF-R, EGF-R, IGF1-R, NGF-R, FGF-R, Leptin-R (STRO-2=Leptin-R), RANKL, STRO-1$^{bright}$ and CD146 or any combination of these markers.

In one example, the progeny cells are Multipotential Expanded STRO-1$^+$ Multipotential cells Progeny (MEMPs) as defined and/or described in WO 2006/032092. Methods for preparing enriched populations of STRO-1$^+$ multipotential cells from which progeny may be derived are described in WO 01/04268 and WO 2004/085630. In an in vitro context STRO-1$^+$ multipotential cells will rarely be present as an absolutely pure preparation and will generally be present with other cells that are tissue specific committed cells (TSCCs). WO 01/04268 refers to harvesting such cells from bone marrow at purity levels of about 0.1% to 90%. The population comprising MPCs from which progeny are derived may be directly harvested from a tissue source, or alternatively it may be a population that has already been expanded ex vivo.

For example, the progeny may be obtained from a harvested, unexpanded, population of substantially purified STRO-1$^+$ multipotential cells, comprising at least about 0.1, 1, 5, 10, 20, 30, 40, 50, 60, 70, 80 or 95% of total cells of the population in which they are present. This level may be achieved, for example, by selecting for cells that are positive for at least one marker individually or collectively selected from the group consisting of TNAP, STRO-1$^{bright}$, 3G5$^+$, VCAM-1, THY-1, CD146 and STRO-2.

MEMPS can be distinguished from freshly harvested STRO-1$^+$ multipotential cells in that they are positive for the marker STRO-1$^{bri}$ and negative for the marker Alkaline phosphatase (ALP). In contrast, freshly isolated STRO-1$^+$ multipotential cells are positive for both STRO-1$^{bri}$ and ALP. In a preferred example of the present invention, at least 15%, 20%, 30%, 40%, 50%, 60%, 70%, 80%, 90% or 95% of the administered cells have the phenotype STRO-1$^{bri}$, ALP$^-$. In a further preferred example the MEMPS are positive for one or more of the markers Ki67, CD44 and/or CD49c/CD29, VLA-3, α3β1. In yet a further preferred example the MEMPs do not exhibit TERT activity and/or are negative for the marker CD18.

The STRO-1$^+$ cell starting population may be derived from any one or more tissue types set out in WO 01/04268 or WO 2004/085630, namely bone marrow, dental pulp cells, adipose tissue and skin, or perhaps more broadly from adipose tissue, teeth, dental pulp, skin, liver, kidney, heart, retina, brain, hair follicles, intestine, lung, spleen, lymph node, thymus, pancreas, bone, ligament, bone marrow, tendon and skeletal muscle.

It will be understood that in performing the present invention, separation of cells carrying any given cell surface marker can be effected by a number of different methods, however, preferred methods rely upon binding a binding agent (e.g., an antibody or antigen binding fragment thereof) to the marker concerned followed by a separation of those that exhibit binding, being either high level binding, or low level binding or no binding. The most convenient binding agents are antibodies or antibody-based molecules, preferably being monoclonal antibodies or based on monoclonal antibodies because of the specificity of these latter agents. Antibodies can be used for both steps, however other agents might also be used, thus ligands for these markers may also be employed to enrich for cells carrying them, or lacking them.

The antibodies or ligands may be attached to a solid support to allow for a crude separation. The separation techniques preferably maximize the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to FACS. Methods for performing FACS will be apparent to the skilled artisan.

Antibodies against each of the markers described herein are commercially available (e.g., monoclonal antibodies against STRO-1 are commercially available from R & D Systems, USA), available from ATCC or other depositary organization and/or can be produced using art recognized techniques.

It is preferred that the method for isolating STRO-1$^+$ cells, for example, comprises a first step being a solid phase sorting step utilizing for example magnetic activated cell sorting (MACS) recognizing high level expression of STRO-1. A second sorting step can then follow, should that be desired, to result in a higher level of precursor cell expression as described in patent specification WO 01/14268. This second sorting step might involve the use of two or more markers.

The method obtaining STRO-1$^+$ cells might also include the harvesting of a source of the cells before the first enrichment step using known techniques. Thus the tissue will be surgically removed. Cells comprising the source tissue will then be separated into a so called single cells suspension. This separation may be achieved by physical and or enzymatic means.

Once a suitable STRO-1$^+$ cell population has been obtained, it may be cultured or expanded by any suitable means to obtain MEMPs.

In one example, the cells are taken from the subject to be treated, cultured in vitro using standard techniques and used to obtain supernatant or soluble factors or expanded cells for administration to the subject as an autologous or allogeneic composition. In an alternative example, cells of one or more of the established human cell lines are used to obtain the supernatant or soluble factors. In another useful example of the invention, cells of a non-human animal (or if the patient is not a human, from another species) are used to obtain supernatant or soluble factors.

The invention can be practised using cells from any non-human animal species, including but not limited to non-human primate cells, ungulate, canine, feline, lagomorph, rodent, avian, and fish cells. Primate cells with which the invention may be performed include but are not limited to cells of chimpanzees, baboons, cynomolgus monkeys, and any other New or Old World monkeys. Ungulate cells with which the invention may be performed include but are not limited to cells of bovines, porcines, ovines, caprines, equines, buffalo and bison. Rodent cells with which the invention may be performed include but are not limited to mouse, rat, guinea pig, hamster and gerbil cells. Examples of lagomorph species with which the invention may be performed include domesticated rabbits, jack rabbits, hares, cottontails, snowshoe rabbits, and pikas. Chickens (*Gallus gallus*) are an example of an avian species with which the invention may be performed.

Cells useful for the methods of the invention may be stored before use, or before obtaining the supernatant or soluble factors. Methods and protocols for preserving and storing of eukaryotic cells, and in particular mammalian cells, are known in the art (cf., for example, Pollard, J. W. and Walker, J. M. (1997) Basic Cell Culture Protocols, Second Edition, Humana Press, Totowa, N.J.; Freshney, R. I. (2000) Culture of Animal Cells, Fourth Edition, Wiley-Liss, Hoboken, N.J.). Any method maintaining the biological activity of the isolated stem cells such as mesenchymal stem/progenitor cells, or progeny thereof, may be utilized in connection with the present invention. In one preferred example, the cells are maintained and stored by using cryo-preservation.

Genetically-Modified Cells

In one example, the STRO-1$^+$ cells and/or progeny cells thereof are genetically modified, e.g., to express and/or secrete a protein of interest, e.g., a protein providing a therapeutic and/or prophylactic benefit, e.g., insulin, glucagon, somatostatin, trypsinogen, chymotrypsinogen, elastase, carboxypeptidase, pancreatic lipase or amylase or a polypeptide associated with or causative of enhanced angiogenesis or a polypeptide associated with differentiation of a cell into a pancreatic cell or a vascular cell.

Methods for genetically modifying a cell will be apparent to the skilled artisan. For example, a nucleic acid that is to be expressed in a cell is operably-linked to a promoter for inducing expression in the cell. For example, the nucleic acid is linked to a promoter operable in a variety of cells of a subject, such as, for example, a viral promoter, e.g., a CMV promoter (e.g., a CMV-IE promoter) or a SV-40 promoter. Additional suitable promoters are known in the art and shall be taken to apply mutatis mutandis to the present example of the invention.

Preferably, the nucleic acid is provided in the form of an expression construct. As used herein, the term "expression construct" refers to a nucleic acid that has the ability to confer expression on a nucleic acid (e.g. a reporter gene and/or a counter-selectable reporter gene) to which it is operably connected, in a cell. Within the context of the present invention, it is to be understood that an expression construct may comprise or be a plasmid, bacteriophage, phagemid, cosmid, virus sub-genomic or genomic fragment, or other nucleic acid capable of maintaining and/or replicating heterologous DNA in an expressible format.

Methods for the construction of a suitable expression construct for performance of the invention will be apparent to the skilled artisan and are described, for example, in Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001). For example, each of the components of the expression construct is amplified from a suitable template nucleic acid using, for example, PCR and subsequently cloned into a suitable expression construct, such as for example, a plasmid or a phagemid.

Vectors suitable for such an expression construct are known in the art and/or described herein. For example, an expression vector suitable for the method of the present invention in a mammalian cell is, for example, a vector of the pcDNA vector suite supplied by Invitrogen, a vector of the pCI vector suite (Promega), a vector of the pCMV vector suite (Clontech), a pM vector (Clontech), a pSI vector (Promega), a VP 16 vector (Clontech) or a vector of the pcDNA vector suite (Invitrogen).

The skilled artisan will be aware of additional vectors and sources of such vectors, such as, for example, Invitrogen Corporation, Clontech or Promega.

Means for introducing the isolated nucleic acid molecule or a gene construct comprising same into a cell for expression are known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., Wis., USA) amongst others.

Alternatively, an expression construct of the invention is a viral vector. Suitable viral vectors are known in the art and commercially available. Conventional viral-based systems for the delivery of a nucleic acid and integration of that nucleic acid into a host cell genome include, for example, a retroviral vector, a lentiviral vector or an adeno-associated viral vector. Alternatively, an adenoviral vector is useful for introducing a nucleic acid that remains episomal into a host cell. Viral vectors are an efficient and versatile method of gene transfer in target cells and tissues. Additionally, high transduction efficiencies have been observed in many different cell types and target tissues.

For example, a retroviral vector generally comprises cis-acting long terminal repeats (LTRs) with packaging capacity for up to 6-10 kb of foreign sequence. The minimum cis-acting LTRs are sufficient for replication and packaging of a vector, which is then used to integrate the expression construct into the target cell to provide long term expression. Widely used retroviral vectors include those based upon murine leukemia virus (MuLV), gibbon ape leukemia virus (GaLV), simian immunodeficiency virus (SrV), human immunodeficiency virus (HIV), and combinations thereof (see, e.g., Buchscher et al., *J Virol.* 56:2731-2739 (1992); Johann et al, *J. Virol.* 65:1635-1640 (1992); Sommerfelt et al, *Virol.* 76:58-59 (1990); Wilson et al, *J. Virol.* 63:274-2318 (1989); Miller et al., *J. Virol.* 65:2220-2224 (1991); PCT/US94/05700; Miller and Rosman *BioTechniques* 7:980-990, 1989; Miller, A. D. *Human Gene Therapy* 7:5-14, 1990; Scarpa et al *Virology* 75:849-852, 1991; Burns et al. *Proc. Natl. Acad. Sci USA* 90:8033-8037, 1993).

Various adeno-associated virus (AAV) vector systems have also been developed for nucleic acid delivery. AAV vectors can be readily constructed using techniques known in the art. See, e.g., U.S. Pat. Nos. 5,173,414 and 5,139,941; International Publication Nos. WO 92/01070 and WO 93/03769; Lebkowski et al. *Molec. Cell. Biol.* 5:3988-3996, 1988; Vincent et al. (1990) Vaccines 90 (Cold Spring Harbor Laboratory Press); Carter *Current Opinion in Biotechnology* 5:533-539, 1992; Muzyczka. *Current Topics in Microbiol, and Immunol.* 158:97-129, 1992; Kotin, Human Gene Therapy 5:793-801, 1994; Shelling and Smith *Gene Therapy* 7:165-169, 1994; and Zhou et al. *J Exp. Med.* 179:1867-1875, 1994.

Additional viral vectors useful for delivering an expression construct of the invention include, for example, those derived from the pox family of viruses, such as vaccinia virus and avian poxvirus or an alphavirus or a conjugate virus vector (e.g. that described in Fisher-Hoch et al., *Proc. Natl Acad. Sci. USA* 56:317-321, 1989).

Assaying Therapeutic/Prophylactic Potential of Cells and Soluble Factors

Methods for determining the ability of cells or soluble factors to treat or prevent or delay the onset or progression of pancreatic dysfunction will be apparent to the skilled artisan.

For example, cells or soluble factors (e.g., a mixture of factors or a single factor or a fraction of factors (e.g., derived by affinity purification or chromatography)) are administered to a test subject, e.g., a test animal for a time and under conditions sufficient to provide a therapeutic/prophylactic benefit and resting or basal or fasting glucose levels assessed and/or a glucose tolerance test performed. Such tests are performed using commercially available kits and/or devices. Basal or fasting glucose levels are assessed following fasting, e.g., for about 8 to about 14 hours. For a glucose tolerance test, a subject fasts for about 8 to about 14 hours and then consumes glucose (e.g., about 1.75 grams of glucose per kilogram of body weight) and the level of blood glucose assessed after about 2 to 3 hours. According to the World Health Organization, fasting plasma glucose should be below 6.1 mmol/l (100 mg/dl). Fasting levels between 6.1 and 7.0 mmol/l (100 and 126 mg/dl) are borderline ("impaired fasting glycaemia"), and fasting levels repeatedly at or above 7.0 mmol/l (126 mg/dl) are diagnostic of diabetes. The 2 hour glucose level should be below 7.8 mmol/l (140 mg/dl). Levels between this and 11.1 mmol/l (200 mg/dl) indicate impaired glucose tolerance. Glucose levels above 11.1 mmol/l (200 mg/dl) at 2 hours confirms a diagnostic of diabetes.

Preferably, the test subject suffers from pancreatic dysfunction. For example, the test subject is a non-obese diabetic (NOD) mouse (a model of Type I diabetes) or a mouse or rat to which streptozotocin has been administered (models of Type I and/or Type II diabetes; see Lúkic et al., *Developmental Immunol.* 6: 119-128, 1998 and Arulmozhi et al., *Indian J. Pharmacol.*, 36: 217-221, 2004), Goto Kakizaki (GK) rat (model of Type II diabetes), New Zealand Obese (NZO) mouse (model of Type II diabetes). Other models of Type I and/or Type II diabetes are described in, for example, Rees and Alcolado, *Diabet. Med.* 22:359-70, 2005.

Cells and/or soluble factors that reduce basal glucose levels and/or improve glucose tolerance in such a model of pancreatic dysfunction compared to an untreated animal or the test animal prior to treatment are considered likely to treat or prevent or delay the onset or progression of pancreatic dysfunction.

Alternatively, or in addition insulin levels are assessed in the circulation of a test subject, e.g., using an enzyme-linked or fluorescence-linked immunosorbent assay. Cells and/or soluble factors that increase insulin levels in the circulation of a test subject are considered likely to treat or prevent or delay the onset or progression of pancreatic dysfunction.

Kits and assays for determining serum glucagon or somatostatin levels are known in the art and/or commercially available, e.g., from Immuno-Biological Laboratories, Inc or Millipore Corporation.

Alternatively, or in addition, a serum level of amylase is determined using a colorimetric assay, e.g., as described in Caraway, *Am. J. Clin. Pathol.*, 32: 97-99, 1959 or a fluorometric assay, e.g., as described in Rinderknecht and Marbach, *Clin. Chem. Acta.*, 29: 107-110, 1972. Factors or cells that maintain serum amylase levels to normal levels (e.g., 21-101 U/L) are considered likely to treat or prevent or delay the onset or progression of pancreatic dysfunction.

Amylase levels may also be determined in sections of pancreas or in pancreatic juice, e.g., obtained by peroral duodenal intubation. These samples also provide samples for measuring levels of trypsinogen, chymotrypsinogen, elastase, carboxypeptidase, pancreatic lipase. For example, Connon et al., *Digestive Diseases and Sciences,* 23: 472-475, 1978 describe an assay for determining pancreatic lipase levels in pancreatic juice.

The assays described in the previous paragraphs are also suitable for ongoing monitoring of a subject receiving a treatment as described herein according to any example.

It will be apparent to the skilled artisan from the foregoing that the present invention also provides a method for identifying or isolating a cell or a soluble factor for the treatment of pancreatic dysfunction, said method comprising:
(i) administering a cell or a soluble factor to a test subject suffering from pancreatic dysfunction and assessing the pancreatic function of the subject;
(ii) comparing the pancreatic function of the subject at (i) to the pancreatic function of a control subject suffering from pancreatic dysfunction to which the cell or soluble factor has not been administered,
wherein improved pancreatic function in the test subject compared to the control subject indicates that the cell or soluble factor treats pancreatic dysfunction.

The present invention also provides a method for identifying or isolating a cell or a soluble factor for the prevention or delay of pancreatic dysfunction, said method comprising:
(i) administering a cell or a soluble factor to a test subject and then inducing pancreatic dysfunction in the test subject;
(ii) comparing the pancreatic function of the subject at (i) to the pancreatic function of a control subject suffering from pancreatic dysfunction to which the cell or soluble factor has not been administered, wherein improved pancreatic function in the test subject compared to the control subject indicates that the cell or soluble factor prevents or delays the onset of pancreatic dysfunction.

The cell may be any cell described herein according to any example.

Cellular Compositions

In one example of the present invention STRO-1$^+$ cells and/or progeny cells thereof are administered in the form of a composition. Preferably, such a composition comprises a pharmaceutically acceptable carrier and/or excipient.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for this invention include those conventionally used, e.g., water, saline, aqueous dextrose, lactose, Ringer's solution, a buffered solution, hyaluronan and glycols are preferred liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

In another example, a carrier is a media composition, e.g., in which a cell is grown or suspended. Preferably, such a media composition does not induce any adverse effects in a subject to whom it is administered.

Preferred carriers and excipients do not adversely affect the viability of a cell and/or the ability of a cell to reduce, prevent or delay pancreatic dysfunction.

In one example, the carrier or excipient provides a buffering activity to maintain the cells and/or soluble factors at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors, in such a case, the composition of the invention may be produced as a liquid for direct application to the blood stream or into a tissue or a region surrounding or adjacent to a tissue, e.g., by injection.

STRO-1$^+$ cells and/or progeny cells thereof can also be incorporated or embedded within scaffolds that are recipient-compatible and which degrade into products that are not harmful to the recipient. These scaffolds provide support and protection for cells that are to be transplanted into the recipient subjects. Natural and/or synthetic biodegradable scaffolds are examples of such scaffolds.

A variety of different scaffolds may be used successfully in the practice of the invention. Preferred scaffolds include, but are not limited to biological, degradable scaffolds. Natural biodegradable scaffolds include collagen, fibronectin, and laminin scaffolds. Suitable synthetic material for a cell transplantation scaffold should be able to support extensive cell growth and cell function. Such scaffolds may also be resorbable. Suitable scaffolds include polyglycolic acid scaffolds, e.g., as described by Vacanti, et al. *J. Ped. Surg.* 23:3-9 1988; Cima, et al. *Biotechnol. Bioeng.* 38:145 1991; Vacanti, et al. *Plast. Reconstr. Surg.* 88:753-9 1991; or synthetic polymers such as polyanhydrides, polyorthoesters, and polylactic acid.

In another example, the cells may be administered in a gel scaffold (such as Gelfoam from Upjohn Company.

The cellular compositions useful for the present invention may be administered alone or as admixtures with other cells. Cells that may be administered in conjunction with the compositions of the present invention include, but are not limited to, other multipotent or pluripotent cells or stem cells, or bone marrow cells. The cells of different types may be admixed with a composition of the invention immediately or shortly prior to administration, or they may be co-cultured together for a period of time prior to administration.

Preferably, the composition comprises an effective amount or a therapeutically or prophylactically effective amount of cells. For example, the composition comprises about $1 \times 10^5$ STRO-1$^+$ cells/kg to about $1 \times 10^7$ STRO-1$^+$ cells/kg or about $1 \times 10^6$ STRO-1$^+$ cells/kg to about $5 \times 10^6$ STRO-1$^+$ cells/kg. The exact amount of cells to be administered is dependent upon a variety of factors, including the age, weight, and sex of the patient, and the extent and severity of the pancreatic dysfunction.

In some examples, cells are contained within a chamber that does not permit the cells to exit into a subject's circulation, however that permits factors secreted by the cells to enter the circulation. In this manner soluble factors may be administered to a subject by permitting the cells to secrete the factors into the subject's circulation. Such a chamber may equally be implanted at a site in a subject to increase local levels of the soluble factors, e.g., implanted in or near a pancreas.

In some examples of the invention, it may not be necessary or desirable to immunosuppress a patient prior to initiation of therapy with cellular compositions. Accordingly, transplantation with allogeneic, or even xenogeneic, STRO-1$^+$ cells or progeny thereof may be tolerated in some instances.

However, in other instances it may be desirable or appropriate to pharmacologically immunosuppress a patient prior to initiating cell therapy. This may be accomplished through the use of systemic or local immunosuppressive agents, or it may be accomplished by delivering the cells in an encapsulated device. The cells may be encapsulated in a capsule that is permeable to nutrients and oxygen required by the cell and therapeutic factors the cell is yet impermeable to immune humoral factors and cells. Preferably the encapsulant is hypoallergenic, is easily and stably situated in a target tissue, and provides added protection to the implanted structure. These and other means for reducing or eliminating an immune response to the transplanted cells are known in the art. As an alternative, the cells may be genetically modified to reduce their immunogenicity.

Compositions of Soluble Factors

In one example of the present invention, STRO-1$^+$ cell-derived and/or progeny cell-derived supernatant or soluble factors are administered in the form of a composition, e.g., comprising a suitable carrier and/or excipient. Preferably, the carrier or excipient does not adversely affect the biological effect of the soluble factors or supernatant.

In one example, the composition comprises a composition of matter to stabilize a soluble factor or a component of supernatant, e.g., a protease inhibitor. Preferably, the protease inhibitor is not included in an amount sufficient to have an adverse effect on a subject.

Compositions comprising STRO-1+ cell-derived and/or progeny cell-derived supernatant or soluble factors may be prepared as appropriate liquid suspensions, e.g., in culture medium or in a stable carrier or a buffer solution, e.g., phosphate buffered saline. Suitable carriers are described herein above. In another example, suspensions comprising STRO-1+ cell-derived and/or progeny cell-derived supernatant or soluble factors are oily suspensions for injection. Suitable lipophilic solvents or vehicles include fatty oils such as sesame oil; or synthetic fatty acid esters, such as ethyl oleate or triglycerides; or liposomes. Suspensions to be used for injection may also contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Sterile injectable solutions can be prepared by incorporating the supernatant or soluble factors in the required amount in an appropriate solvent with one or a combination of ingredients described above, as required, followed by filtered sterilization.

Generally, dispersions are prepared by incorporating the supernatant or soluble factors into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, the supernatant or soluble factors may be formulated with one or more additional compounds that enhance its solubility.

Other exemplary carriers or excipients are described, for example, in Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.

Therapeutic compositions typically should be sterile and stable under the conditions of manufacture and storage. The composition can be formulated as a solution, microemulsion, liposome, or other ordered structure. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the soluble factors may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

The supernatant or soluble factors may be administered in combination with an appropriate matrix, for instance, to provide slow release of the soluble factors.

Additional Components of Compositions

The STRO-1+ cell-derived supernatant or soluble factors, STRO-1+ cells or progeny thereof may be administered with other beneficial drugs or biological molecules (growth factors, trophic factors). When administered with other agents, they may be administered together in a single pharmaceutical composition, or in separate pharmaceutical compositions, simultaneously or sequentially with the other agents (either before or after administration of the other agents). Bioactive factors which may be co-administered include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPDXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., antithymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine) as well as local anesthetics.

In one example, a composition as described herein according to any example comprises an additional factor for the treatment or prophylaxis of a pancreatic dysfunction. For example, the composition comprises a biguanide, a thiazolidinedione, a sulfonylurea, a benzoic acid derivative, an alpha-glucosidase inhibitor, a SGLT2 inhibitor, and INGAP peptide, a dipeptidyl peptidase-IV inhibitor, an insulin sensitizers (e.g., a PPAR agonist or a biguanide), insulin, an insulin mimetic, a glucagon receptor antagonist, a GLP-I, a GLP-I mimetic, a GLP-I receptor agonists; GIP, a GIP mimetic, a GIP receptor agonist, PACAP, a PACAP mimetics, a PACAP receptor 3 agonist; a cholesterol lowering agent (e.g., HMG-CoA reductase inhibitor, a sequestrant, a nicotmyl alcohol, a nicotinic acid), a PPARα/γ dual agonist or an anti-obesity compound.

In another example, a composition as described herein according to any example additionally comprises a factor that induces or enhances differentiation of a progenitor cell into a pancreatic cell. Exemplary factors include, Wnt, epidermal growth factor, fibroblast growth factor or TGFβ.

In another example, a composition as described herein according to any example additionally comprises a factor that induces or enhances differentiation of a progenitor cell into a vascular cell. Exemplary factors include, vascular endothelial growth factor (VEGF), platelet derived growth factor (PDGF; e.g., PDGF-BB), and FGF.

In another example, a composition as described herein according to any example additionally comprises a tissue specific committed cell (TSCC). In this respect, International Patent Application No. PCT/AU2005/001445 demonstrates that administration of a TSCC and a STRO-1+ cells can lead to enhanced proliferation of the TSCC. In one example, the TSCC is a pancreatic cell, e.g., a β cell or a mixture of pancreatic cells, e.g., an islet of Langerhans. Administration of such a composition to a subject may lead to increased production of, for example, β cells islets of Langerhans In another example, the TSCC is a vascular cell. Administration of such a composition to a subject may lead to increased production of vasculature, e.g., in a pancreas, e.g., leading to increased nutrients being delivered to the pancreas.

Medical Devices

The present invention also provides medical devices for use or when used in a method as described herein according to any example. For example, the present invention provides a syringe or catheter or other suitable delivery device comprising STRO-1+ cells and/or progeny cells thereof and/or soluble factors therefrom and/or a composition of the invention. Optionally, the syringe or catheter is packaged with instructions for use in a method as described herein according to any example.

In another example, the present invention provides an implant comprising STRO-1¹ cells and/or progeny cells thereof and/or soluble factors therefrom and/or a composition of the invention. Optionally, the implant is packaged with instructions for use in a method as described herein according to any example. Suitable implants may be formed with a scaffold, e.g., as described herein above and STRO-1+ cells and/or progeny cells thereof and/or soluble factors therefrom.

Modes of Administration

The STRO-1¹ cell-derived supernatant or soluble factors, STRO-1¹ cells or progeny thereof may be surgically implanted, injected, delivered (e.g., by way of a catheter or syringe), or otherwise administered directly or indirectly to the site in need of repair or augmentation, e.g., a pancreas or into the blood system of a subject.

Preferably, the STRO-1+ cell-derived supernatant or soluble factors, STRO-1+ cells or progeny thereof is delivered to the blood stream of a subject. For example, the STRO-1+ cell-derived supernatant or soluble factors, STRO-1+ cells or progeny thereof are delivered parenterally. Exemplary routes of parenteral administration include, but are not limited to, intraperitoneal, intraventricular, intracerebroventricular, intrathecal. Preferably, the STRO-1+ cell-derived supernatant or soluble factors, STRO-1+ cells or progeny thereof are delivered intra-arterially, into an aorta, into an atrium or ventricle of the heart or into a blood vessel connected to a pancreas, e.g., an abdominal aorta, a superior mesenteric artery, a pancreaticoduodenal artery or a splenic artery. In another example, STRO-1+ cell-derived supernatant or soluble factors, STRO-1+ cells or progeny thereof are administered to a femoral artery or a celiac artery.

In the case of cell delivery to an atrium or ventricle of the heart, it is preferred that cells are administered to the left atrium or ventricle to avoid complications that may arise from rapid delivery of cells to the lungs.

Preferably, the STRO-1+ cell-derived supernatant or soluble factors, STRO-1+ cells or progeny thereof are injected into the site of delivery, e.g., using a syringe or through a catheter or a central line.

Selecting an administration regimen for a therapeutic formulation depends on several factors, including the serum or tissue turnover rate of the entity, the level of symptoms, and the immunogenicity of the entity. Preferably, an administration regimen maximizes the amount of therapeutic compound delivered to the patient consistent with an acceptable level of side effects. Accordingly, the amount of formulation delivered depends in part on the particular entity and the severity of the condition being treated.

In one example, STRO-1+ cell-derived supernatant or soluble factors, STRO-1+ cells or progeny thereof are delivered as a single bolus dose. Alternatively, STRO-1+ cell-derived supernatant or soluble factors, STRO-1+ cells or progeny thereof are administered by continuous infusion, or by doses at intervals of, e.g., one day, one week, or 1-7 times per week. A preferred dose protocol is one involving the maximal dose or dose frequency that avoids significant undesirable side effects. A total weekly dose depends on the type and activity of the compound being used. Determination of the appropriate dose is made by a clinician, e.g., using parameters or factors known or suspected in the art to affect treatment or predicted to affect treatment. Generally, the dose begins with an amount somewhat less than the optimum dose and is increased by small increments thereafter until the desired or optimum effect is achieved relative to any negative side effects. Important diagnostic measures include those of symptoms of diabetes.

In accordance with examples of the invention directed to treating or delaying the progression of pancreatic dysfunction, it is preferred that the STRO-1+ cells and/or progeny cells thereof and/or soluble factors derived therefrom are administered following diagnosis of the disorder, e.g., using standard methods known in the art and/or described herein, e.g., glucose tolerance.

For those examples directed to preventing or delaying the onset of pancreatic dysfunction, it is preferred that the STRO-1+ cells and/or progeny cells thereof and/or soluble factors derived therefrom are administered prior to clinical diagnosis of the disorder, e.g., when the subject suffers from impaired glucose tolerance and/or impaired fasting glycemia and/or in the case of Type I diabetes prior to or concomitant with an autoimmune response such as indicated by expansion of a population of T cells and/or B cells and/or by the production of autoantibodies (e.g., expansion of cytotoxic T cells against pancreatic β-islet cells and/or autoantibodies against one or more pancreatic β-islet cell markers in the onset or progression of type 1 diabetes). Methods for determining or predicting the onset of an autoimmune response will be apparent to the skilled person and/or described herein. For example, the detection of an auto-antibody against an antigen derived from or on the surface of a pancreatic β-cell is indicative of an immune response against said cell by a subject. One such assay detects islet cell antibodies in the serum of a subject. This assay comprises contacting a section of a pancreas comprising an islet cell with scrum from a test subject. Immunoglobulin in the serum from the subject that is capable of binding to a pancreatic β-islet cell is then detected using a secondary labeled antibody that binds to human immunoglobulin. A suitable method for detecting islet cell antibodies using a fluorescent marker is described, for example, in Bottazzo et al, Lancet 2: 1279-83, 1974. Alternatively, or in addition, an assay is used to detect an auto-antibody that binds to a specific antigen in a subject. By way of example, Brooking et al. (Clin Chim Acta 331:55-59, 2003) describe an ELISA based assay for the detection of auto-antibodies against GAD65. The described assay uses a low concentration of the GAD antigen on a microtitre plate to capture the auto-antibodies in a sample. Biotinylated GAD in the fluid phase is added and is captured by the second binding site of the autoantibody, and it is the biotinylated GAD65 that is detected to produce a non-isotopic detectable signal. Nagata et al, *Ann. New York Acad. Sci* 1037: 10-15, 2004 describe an ELISPOT assay useful for detecting the presence of auto-antibodies against insulin, IA-2 and GAD65.

Methods for Monitoring Therapy/Prophylaxis

Methods for monitoring therapy/prophylaxis will be apparent to the skilled artisan based on the description herein. For example, blood glucose levels and/or insulin levels and/or amylase levels are assessed using methods known in the art and/or described herein.

In another example, a sample of pancreas (e.g., a biopsy) is obtained following treatment and the number of beta cells (e.g., cells expressing insulin) and/or alpha cells (e.g., cells expressing glucagon) and/or islets and/or PDX-1 expressing cells, e.g., using immunohistochemisty, immunofluorescence or a nucleic acid amplification assay, e.g., polymerase chain reaction (PCR). Such assays are described herein.

The present invention is described further in the following non-limiting examples.

Example 1

Treatment of Dibetic Mice With STRO-1$^+$ Cells 1.1 Materials and Methods
Streptozotocin (STZ)-Induced Diabetes in Mice Male immunodeficient NOD/scid mice (NOD.CB17-Prkdc$^{scid}$/J; Animal Research Centre, Perth, Australia) at 7-8 weeks of age were injected intraperitoneally (i.p.) with 35 mg/kg of the beta-cell toxin, Streptozotocin (STZ; Sigma-Aldrich, St. Louis, Mo.) daily on days 1-4 after a 4-h morning fast. STZ was dissolved in sodium citrate buffer, pH 4.5, and injected within 15 min of preparation. The mice were maintained under sterile conditions.

Infusion of Cells and Treatment Groups

Immunomagnetically selected human STRO-1$^+$ stromal cells from banked bone marrow cells were culture expanded essentially as described by Gronthos and Zannetino (*Methods Mol Biol.* 449:45-57, 2008) and obtained from Angioblast Systems, USA. Passage 4, STRO-1$^+$ stromal cells cryopreserved in ProFreeze™-CDM (Lonza, USA) were thawed and 2.5×10$^6$ cells were constituted in 200 µl of vehicle per mouse for immediate injection. At day 10, post-STZ treatment, NOD/scid mice were either injected with a single dose of cells through the chest wall into the left ventricle (arterial route) of anaesthetized mice. Control mice were injected with 200 µl of vehicle (ProFreeze™-CDM containing 7.5% DMSO and alpha-MEM) through the arterial or venous routes.

Assays for Blood Glucose and Insulin

Blood glucose was assayed in tail-vein blood with a glucometer (Optimum Xceed™ Diabetes Monitoring System; Abbott Diagnostics, Victoria, Australia) after a 4-h morning fast. Blood insulin was assayed on blood obtained by intracardiac puncture of anesthetized mice before they were killed on day 32 by using a mouse-specific ELISA kit (Ultrasensitive Mouse Insulin ELISA Mercodia, Uppsala, Sweden).

Preparation of Tissue Samples

Animals were euthanized by cervical dislocation and the pancreas was removed and dissected symmetrically, with one half fixed in 10% neutral formalin and the other embedded in Tissue-Tek OCT Compound (Sakura Finetek, Torrance, Calif.) and frozen on dry-ice and stored at −70° C. While the pancreas was specifically used for majority of the analysis in this study, other tissues such as lung, liver, heart, spleen, stomach, intestine/caecum, bladder, testis and brain were collected for histopathology.

Histology and Immunofluorescence Staining of Pancreatic Tissue

For histology of pancreas formalin-fixed paraffin embedded (FFPE) sections were stained with haematoxylin and eosin (H & E). FFPE tissue sections (5 µm) mounted on glass microscope slides were deparaffinised and subject to antigen retrieval by heating in citrate buffer in a pressure cooker. Following antigen retrieval sections were blocked with 10% normal goat serum for 2 h and used for immunofluorescence detection using the following antibodies that have been previously tested and demonstrated to detect mouse-specific molecules in antigen retrieved tissues: guinea-pig anti-insulin (1:100; Millipore, USA), mouse anti-glucagon (10 µg/ml; clone K79bB10; AbCAM), mouse anti-PDX-1 (10 µg/ml; clone 267712; R & D Systems). After the primary antibody incubation step of 2 h, slides were washed three times for 5 min with 0.1% normal goat serum/PBS and incubated for a further 90 min at room temperature with species-specific secondary antibodies (1:400; Goat anti-mouse Alexa Fluor 555; Molecular Probe or Goat-anti-Guinea-pig Rhodamine; Jackson Laboratories or Goat anti-mouse IgG1-FITC; AbCAM). Controls included omitting the primary antibody. The staining of smooth muscle actin (SMA) in pancreatic tissues was performed by direct immunofluorescence using a mouse anti-SMA-FITC mAb (2 mg/ml; clone 1A4; AbCAM).

Assessment of Immunostaining

Slides were viewed in a Zeiss Observer Z1 microscope (Germany) and images were photographed using an Axio-Cam MRm. Captured images of pancreatic sections stained with H & E or antibodies to insulin, glucagon, PDX-1 and SMA and detected with fluorescent probes were analyzed with the Axio Vision Rel 4.7 software. Each 5 mm H & E section from each experimental animal was used to count total number of islets and analyzed for islet size (area and diameter measurements) and normalized to each respective total sectional area measured by image analysis. In addition, each antigen retrieved 5 µm FFPE section stained with anti-insulin, glucagon or PDX-1 antibody were counted for total number of positively stained cells and normalized to the respective measured total sectional area or total islet area. The distribution of pancreatic microvessels of varying diameters were counted and measured by image analysis and normalized to their respective sectional area examined. All images were analyzed at objective magnifications of 20-40×.

RNA Analysis by Semi-Quantitative RT-PCR

RNA samples from the pancreases of experimental groups were extracted in Trizol reagent from a total of 100 mm sections from each frozen tissue. The Trizol tissue extracts were purified for RNA using illustra RNAspin Mini RNA Isolation Kit (GE Healthcare, UK). Total RNA was quantified spectrophotometrically and 1 µg was reverse-transcribed with oligo-dT (pdT$_{12-18}$) and MMLV reverse transcriptase. The cDNA samples were PCR amplified using primers to murine genes for MafA, Ngn3, and Pdx-1 using Tth Plus DNA polymerase (Roche Applied Science) under amplification conditions specified Table 1. The beta-actin gene was used to normalize target gene expression. PCR products were quantified by densitometric analysis of bands visualized under UV-illumination using Kodak ID 3.5 software.

TABLE 1

PCR conditions

| gene | product bp | cycling conditions | cycles |
| --- | --- | --- | --- |
| Actin | 238 | 94° C. 1 min/55° C. 30 sec/72° C. 30 sec | 28 |
| NGN3 | 347 | 94° C. 1 min/55° C. 30 sec/72° C. 30 sec | 45 |
| MafA | 393 | 94° C. 1 min/58° C. 30 sec/72° C. 30 sec | 45 |
| PDX-1 | 243 | 94° C. 1 min/55° C. 30 sec/72° C. 30 sec | 30 |

Statistical Analyses

Student's T-Test was used for P values.

1.2 Results

Streptozotocin-Induced Hyperglycemia in NOD/Scid Mice

Hyperglycaemia was induced in NOD/scid mice by four daily intraperitoneal injections of STZ 35 mg/kg/day. At day 1 of the study, i.e. prior to the first STZ injection, the mean fasting blood glucose level (BGL) for the whole group of animals (N=80) was 7 mM+/−1.5 standard deviations (SD). Animals were considered to develop hyperglycemia if they had a BGL at day 10 of the study (i.e. 5 days after completion of the STZ course) that was greater than 3SD above the mean glucose level in untreated mice. Mice which did not achieve hyperglycemia according to this criterion were subsequently excluded from all analyses. There were 29 mice who met the above criterion for hyperglycemia at day 10. In these mice, mean BGL at day 10 were 15.2 mM+/−0.6, an increase of 217% above baseline.

Effect of Intra-Arterial Injection of STRO-1$^+$ Stromal Cells on Blood Glucose Levels in Diabetic NOD/Scid Mice As shown in FIG. 1, a single dose of $2.5\times10^6$ STRO-1$^+$ cells injected into hyperglycaemic mice by the intra-arterial route resulted in reduced BGL throughout the course of 3 weeks following cell therapy.

FIG. 1 shows that a single intra-arterial injection of STRO-1$^+$ cells induced early reduction in BGL in diabetic mice in comparison to intra-arterial injection of the vehicle alone. Reduction in BGL was evident as early as day 17, was maximal at day 24 (35% mean reduction, mean BGL 12.7 mM+/−1.2 vs 19.6 mM+/−2.1; p=0.012), and persisted throughout the three weeks of follow-up.

Figure 2:
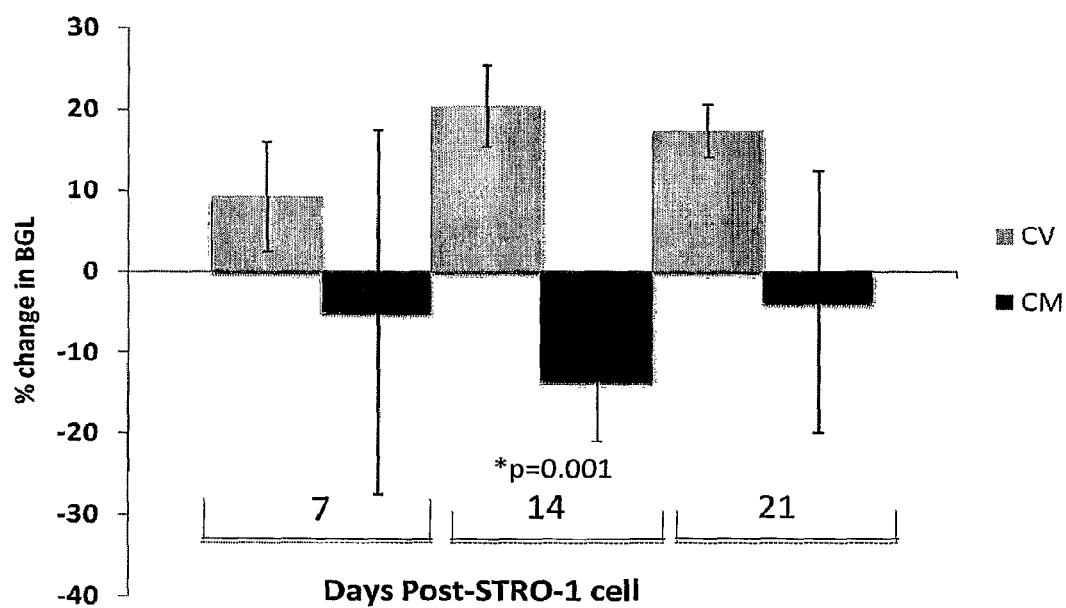
FIG. 2 is a graphical representation showing the effects of STRO-1$^+$ cells on blood glucose levels (BGL) in STZ-induced diabetic NOD/scid mice at 7, 14 and 21 days after treatment compared with baseline at day 10 post-STZ treatment. Blood glucose levels were determined in diabetic mice injected in the left ventricle with vehicle (CV) or with STRO-1$^+$ cells (CM). Results are expressed as % change in BGL relative to the start of cell therapy on day 10. Student's t-test was performed with significance at $p<0.05$.

Single Intra-Arterial Injection of STRO-1$^+$ Cells Results in Early and Persistent Reduction in Blood Glucose Levels Relative to Baseline STZ treated mice receiving a single intra-arterial injection of STRO-1$^+$ cells demonstrated a persistent reduction in mean BGL relative to the level at day 10 baseline throughout the entire three weeks of follow-up. As shown in FIG. 2, this group of animals had mean BGL below pre-therapy levels throughout the entire study period, while media-treated controls demonstrated progressively increased BGL levels. The group receiving an intra-arterial injection of STRO-1$^+$ cells at day 10 post STZ treatment demonstrated mean BGL reductions of −11%, −14%, and −4% relative to baseline BGL at days 7, 14, and 21, respectively. In contrast, the control group receiving intra-arterial media alone demonstrated mean BGL increases of +8%, +20%, and +17% relative to baseline BGL at days 7, 4, and 21, respectively.

Figure 3:
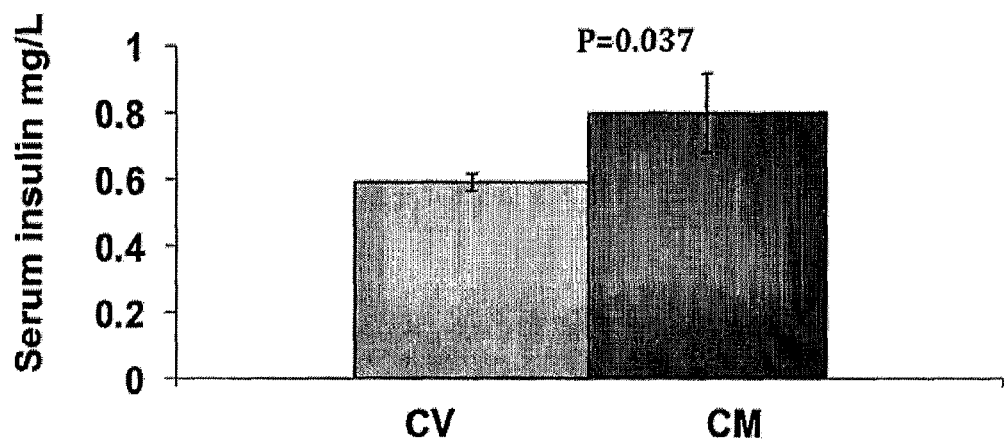
FIG. 3 is a graphical representation showing the effect of STRO-1$^+$ cells on insulin levels in STZ-induced diabetic NOD/scid mice 21 days after cell therapy dose. Serum mouse insulin levels were determined in diabetic mice injected in the left ventricle with vehicle (CV) or with STRO-1$^1$ cells (CM). Mouse insulin values are in µg/L+/−SE. Student's t-test was performed with significance at $p<0.05$.

Single Intra-Arterial Injection of Human STRO-1$^+$ Cells in Diabetic NOD/Scid Mice Results in Significantly Increased Circulating Levels of Mouse Insulin Three Weeks Later As shown in FIG. 3, circulating serum insulin levels measured at day 21 after treatment by a mouse-specific insulin ELISA demonstrated that diabetic mice injected intra-arterially three weeks earlier with STRO-1$^|$ cells had significantly higher circulating endogenous insulin levels in comparison with vehicle-treated diabetic mice (0.79 mg/L+/−0.11 vs 0.57 mg/L+/−0.02; p=0.009).

Figure 4A:
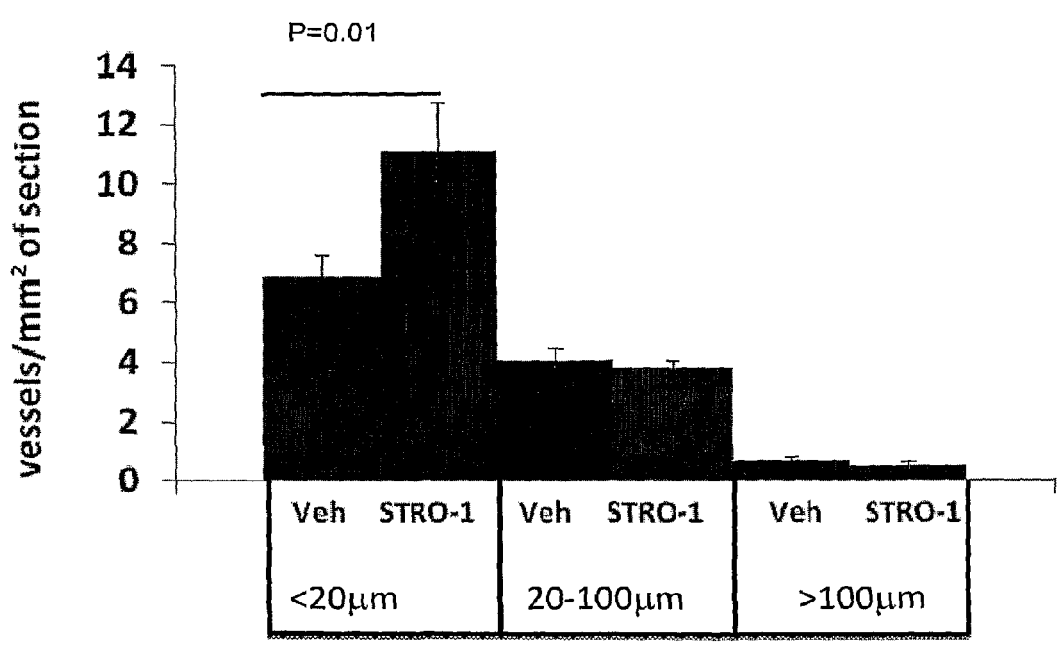
FIG. 4A is a graphical representation showing the effect of intra-arterial STRO-1$^+$ cells on pancreatic microvessel density in STZ-induced diabetic NOD/scid mice 21 days after cell therapy dose. The total numbers of anti-smooth-muscle actin (SMA) stained microvessels were determined based on size distribution per cross-sectional area of pancreatic section. The data represents mean+/−sem; with vehicle group N=8, and STRO-1 therapy N=6 animals. Student's T-Test was performed with significance at $p<0.05$.
Figure 4B:
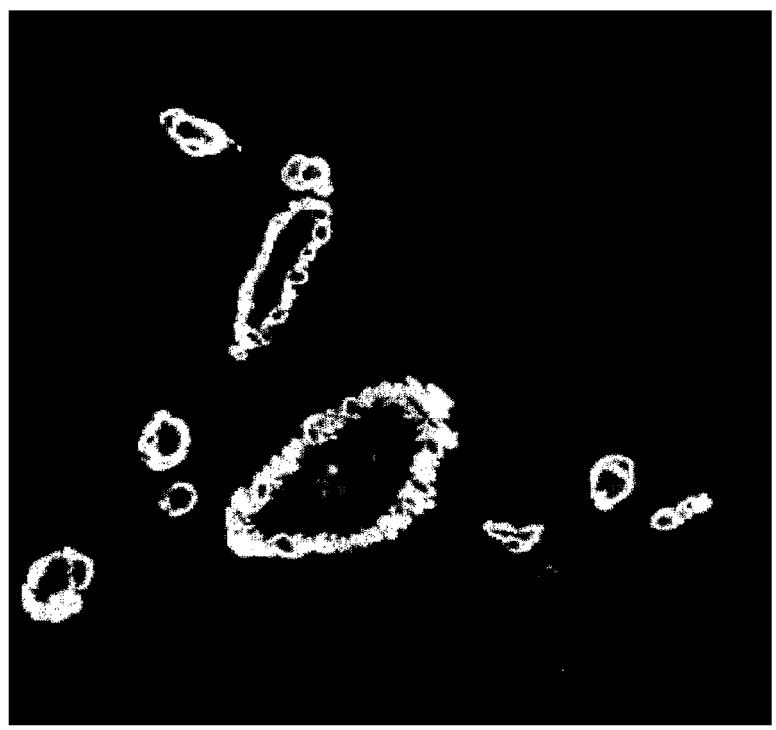
FIG. 4B is a copy of a micrograph (200×) showing mouse anti-smooth muscle actin IgG2a-FITC stained micro-vessels of varying diameters in pancreatic tissue of mice treated with STRO-1 cells.

Single Intra-Arterial Infection of STRO-1$^+$ Cells Results in Increased Pancreatic Microvessel Density in Diabetic NOD/Scid Mice Pancreatic tissues were stained with a directly conjugated monoclonal antibody (mAb) against smooth muscle actin protein to determine whether or not STRO-1$^+$ cell therapy induces arteriogenesis in the damaged pancreas. After immunostaining, the entire section was scanned and the total number of microvessels were counted and normalized to the total sectional area. Vessel numbers were counted and categorized based on size into 3 distinct vessel diameters of <20 μm, 20-100 μm and >100 μm. FIG. 4 shows that there was a 176% increase in the number of smooth muscle actin positive microvessels with diameters<20 μm in the STRO-1$^+$ cell therapy group compared to the vehicle group (299.8+/−52 vs 169.1+/−18.5; p=0.01). Thus, therapy with STRO-1$^|$ cells induces a small caliber arteriolar response within the damaged pancreas.

Figure 5A:
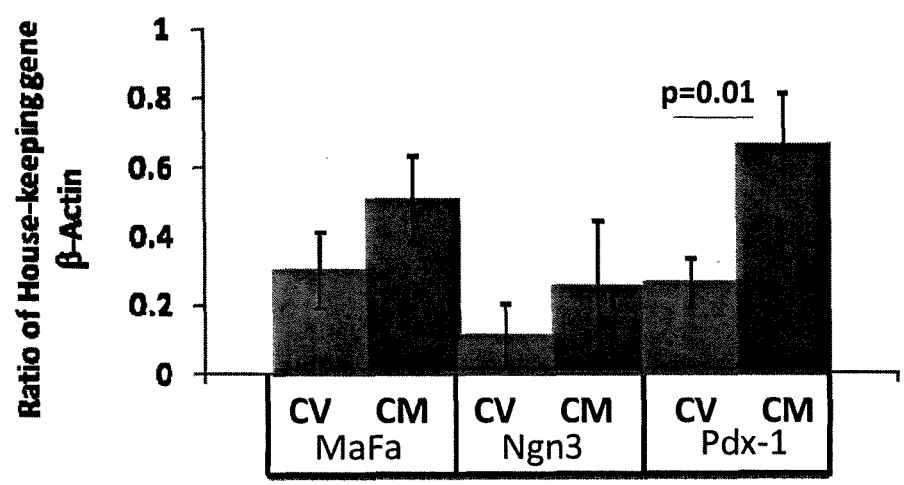
FIG. 5A is a graphical representation showing the effect of intra-arterial STRO-1$^+$ cells on the pancreatic mRNA profile in STZ-induced diabetic NOD/scid mice 21 days after cell therapy dose. RNA was extracted from pancreatic tissue of the vehicle (CV) and STRO-1 therapy (CM) groups, reverse-transcribed and PCR amplified for the transcription factors relevant for beta-cell regeneration: Mafa, Ngn3, Pdx-1. Total RNA content was normalised with respect to the house-keeping gene beta-actin. The data represent mean+/−sem; with vehicle group N=8, and STRO-1 therapy N=6 animals. Student's T-Test was performed with significance at $p<0.05$.

Single Intra-Arterial Injection of STRO-1$^+$ Cells Results in Augmented Pancreatic Expression of the PDX-1 Transcription Factor in Diabetic NOD/Scid Mice To evaluate whether or not human STRO-1$^+$ cell therapy could induce a regenerative response in endogenous beta cells of diabetic NOD/scid mice, mRNA expression levels of the PDX-1, MafA, and Ngn3 transcription factors associated with pancreatic development and beta cell generation (Zhou et al., Nature 455:627-632, 2008) were examined. As shown in FIG. 5A, there was a 2.5 fold increase (p=0.01) in the mean pancreatic mRNA levels for the transcription factor PDX-1 in the STRO-1$^+$ cell therapy group compared to the vehicle group. Increases were also noted in pancreatic mRNA levels for the transcription factors MafA and Ngn3, but these did not reach significance.

Figure 5B:
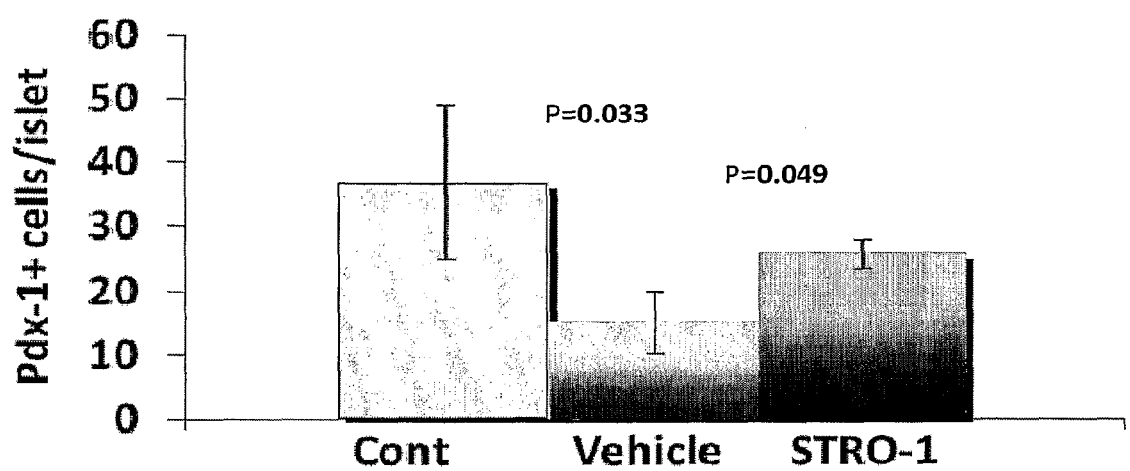
FIG. 5B is a graphical representation showing the effect of intra-arterial STRO-1$^+$ cells on PDX-1 positive cells in STZ-induced diabetic NOD/scid mice 21 days after cell therapy dose. Anti-PDX-1 stained pancreatic tissues were analysed for PDX-1 positive cells per mm$^2$ of islet area. The data represents mean+/−sem; with vehicle group N=8, STRO-1 therapy N=6 and untreated controls (no STZ) N=3 animals. Student's T-Test was performed with significance at $p<0.05$.
Figure 5C:
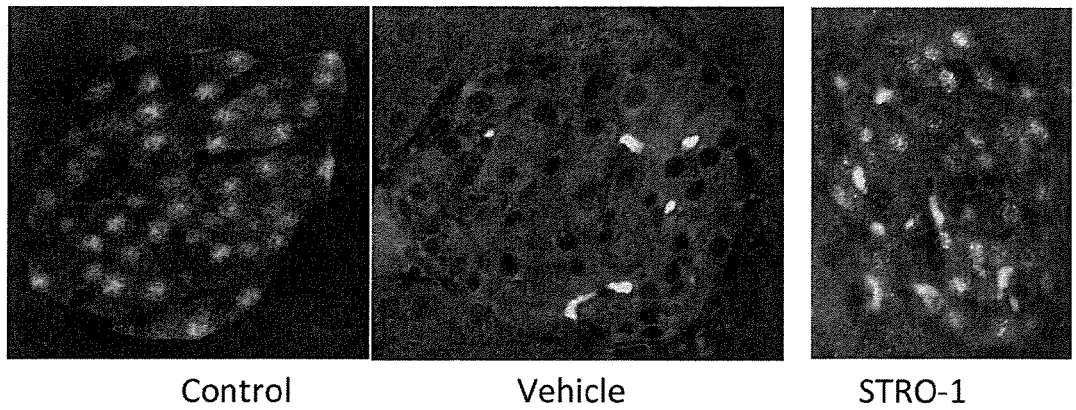
FIG. 5C is a copy of a series of micrographs (400×) showing antigen-retrieved formalin-fixed paraffin embedded sections that were stained with mouse anti-PDX-1 (IgG2b) and detected with goat anti-mouse IgG2b-Alexa 555 conjugate.

To confirm that increased protein levels of the PDX transcription factor were expressed by pancreatic islets exposed to STRO-1$^+$ cell therapy, islet sections from healthy non-diabetic NOD/scid mice, diabetic NOD/scid mice treated with control media, and diabetic NOD/scid mice treated with intra-arterial STRO-1$^+$ cells were immunohistochemically examined using anti-PDX-1 mAb. As shown in FIG. 5B, streptozotocin treatment resulted in 59% reduction in mean number of islet cells that were PDX-1 protein positive compared with healthy non-diabetic mice (37.1+/−12 mean positive cells/islet vs 15.1+/−4.8 mean positive cells/islet, p=0.03). In comparison to streptozotocin-treated animals who received control media, intra-arterial injection of STRO-1$^+$ cells increased the number of islet cells that were PDX-1 protein positive by a mean of 71% (25.7+/−2.2 mean positive cells/islet, p=0.049), resulting in a mean reduction in PDX-1 protein positive cells compared with non-diabetic animals of only 31% (p=NS). The fluorescent photomicrograph in FIG. 5C shows that pancreatic islets from representative NOD/scid animals who were either non-diabetic or who were diabetic and treated with STRO-1$^+$ cells demonstrated similar numbers of PDX-1-positive cells. In contrast, a pancreatic islet from a representative NOD/scid animal who was diabetic and received control media demonstrates significantly reduced numbers of cells that are PDX-1 protein-positive.

Figure 6A:
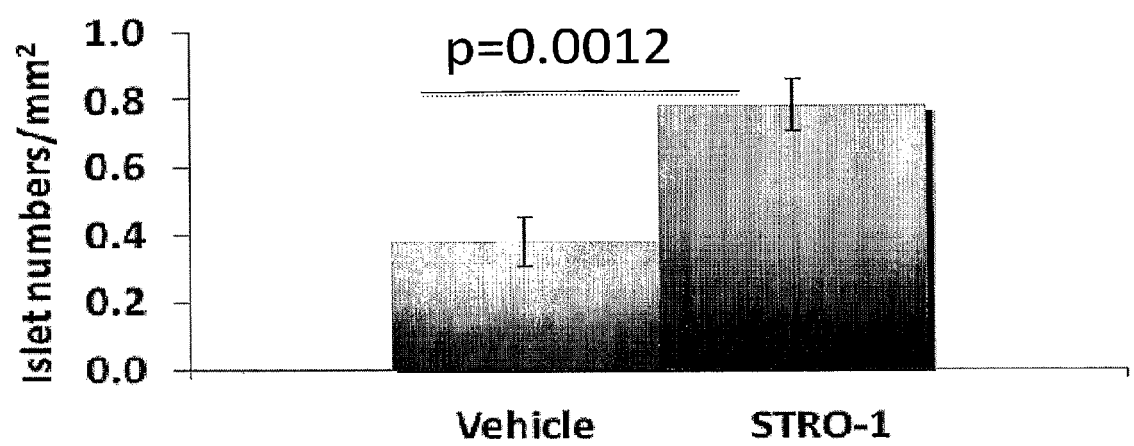
FIG. 6A is a graphical representation showing the effect of intra-arterial STRO-1$^+$ cells on pancreatic islet characteristics in STZ-induced diabetic NOD/scid mice after 21 days of cell therapy. H & E stained pancreatic tissues were analyzed for islet density, which was normalized with respect to examined sectional area. The data represents mean+/−sem; with vehicle group N=8, and STRO-1 therapy N=6 animals. Student's T-Test was performed with significance at $p<0.05$.
Figure 6B:
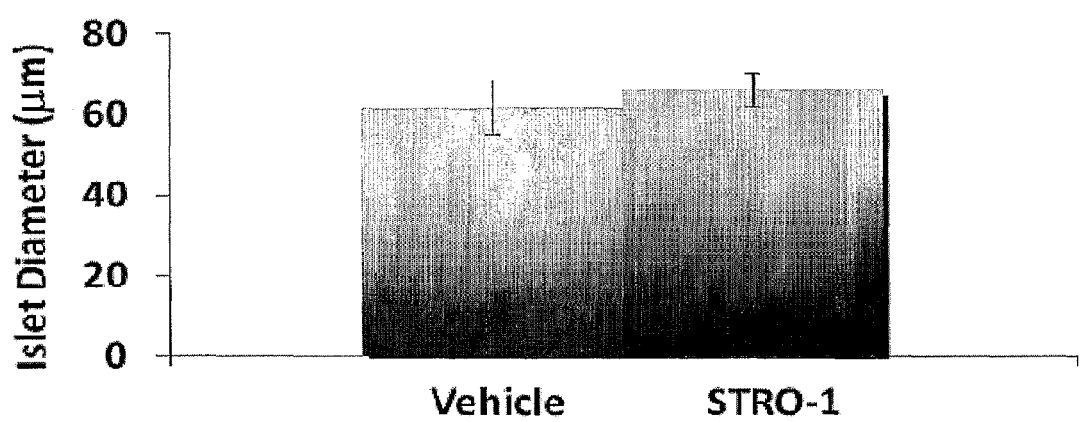
FIG. 6B is a graphical representation showing the effect of intra-arterial STRO-1$^1$ cells on pancreatic islet characteristics in STZ-induced diabetic NOD/scid mice after 21 days of cell therapy. H & E stained pancreatic tissues were analyzed for mean islet diameter, which was normalized with respect to examined sectional area. The data represents mean+/−sem; with vehicle group N=8, and STRO-1 therapy N=6 animals.
Figure 6C:
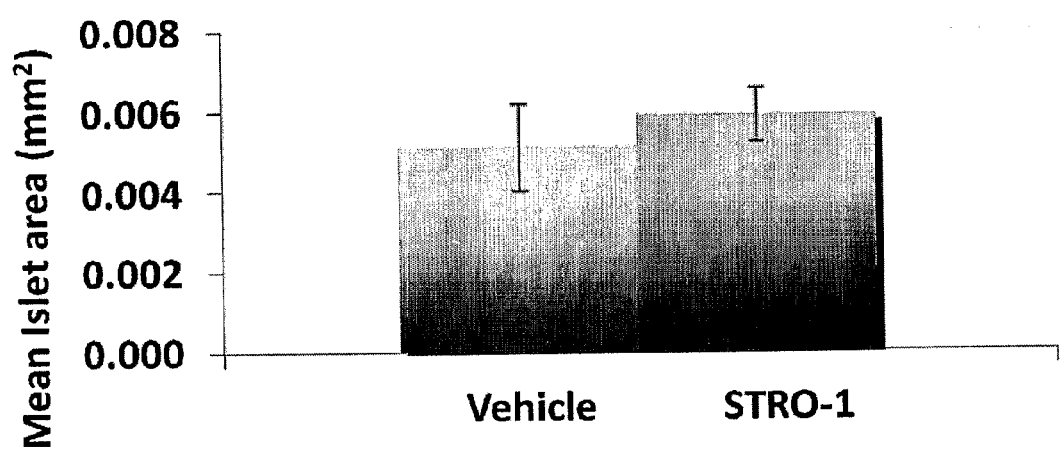
FIG. 6C is a graphical representation showing the effect of intra-arterial STRO-1$^+$ cells on pancreatic islet characteristics in STZ-induced diabetic NOD/scid mice after 21 days of cell therapy. H & E stained pancreatic tissues were analyzed for mean islet area, which was normalized with respect to examined sectional area. The data represents mean+/−sem; with vehicle group N=8, and STRO-1 therapy N=6 animals.

Single Intra-Arterial Injection of STRO-1+ Cells Results in Increased Numbers of Pancreatic Islets The effect of treatment with STRO-1+ cells on total pancreatic islet numbers was also assessed. As shown in FIG. 6A, animals receiving a single intra-arterial injection of STRO-1+ cells three weeks earlier demonstrated at sacrifice over 2-fold greater numbers of pancreatic islets compared with controls injected with media alone (0.78+/−0.07 vs 0.38+/−0.07 islets/mm$^2$, p=0.0012). Other than an increase in total islet numbers, no significant changes were noted in the mean islet diameter or islet area between the treatment groups, FIGS. 6B and 6C.

Figure 7A:
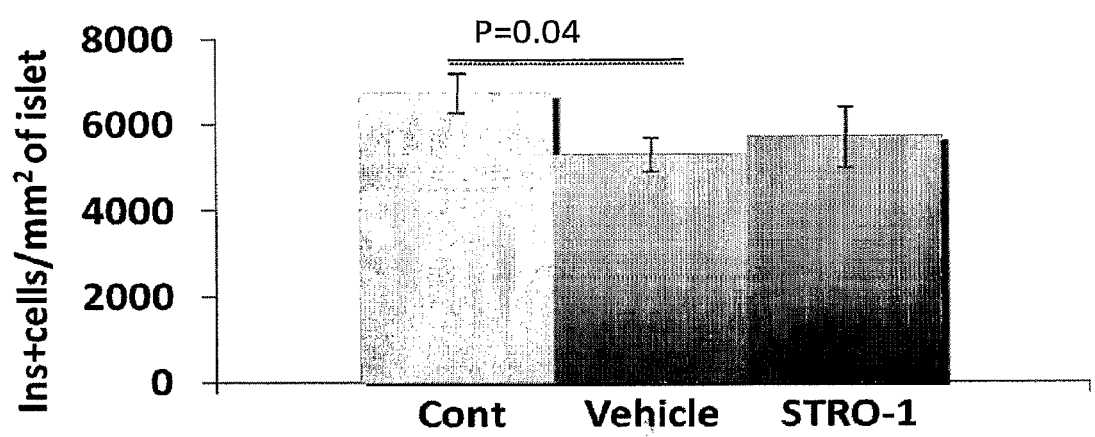
FIG. 7A is a graphical representation showing the effect of intra-arterial STRO-1$^+$ cells on islet characteristics in STZ-induced diabetic NOD/scid mice after 21 days of cell therapy. Anti-insulin stained pancreatic tissues were analyzed for insulin positive cells per mm² of islet area. The data represents mean+/−sem; with vehicle group N=8, STRO-1 therapy N=6 and untreated controls (no STZ) N=3 animals. Student's T-Test was performed with significance at $p<0.05$.
Figure 7B:
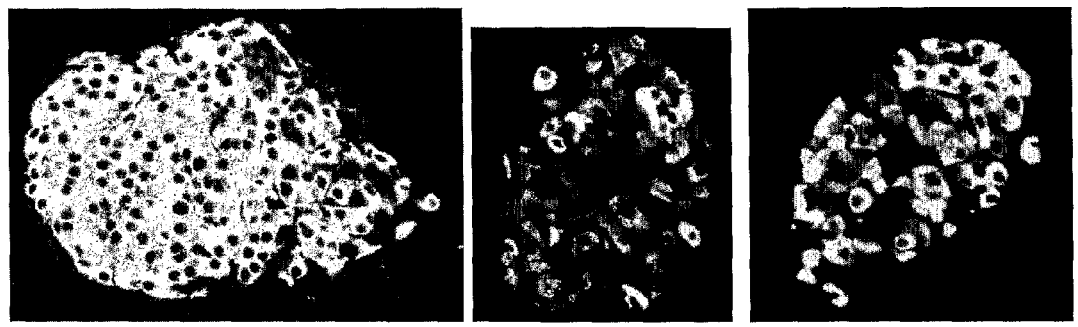
FIG. 7B is a copy of a series of micrographs (200×) showing antigen-retrieved formalin-fixed paraffin embedded sections that were stained with guinea pig anti-insulin and detected with anti-guinea-pig IgG-Rhodamine conjugate. Treatment groups are indicated at the base of each photomicrograph.

Single Intra-Arterial Injection of STRO-1+ Cells Results in Increased Numbers of Endogenous Beta Cells, Reduction in Alpha Cells, and Re-Establishment of a Normal Beta/Alpha Cell Ratio Within the Islets in Diabetic NOD/Scid Mice Anti-mouse insulin mAb staining was used to quantify numbers of beta cells within islets in pancreatic sections of healthy non-diabetic NOD/scid mice, diabetic NOD/scid mice treated with control media, and diabetic NOD/scid mice treated intra-arterially with STRO-1+ cells. As shown in FIG. 7A, streptozotocin treatment resulted in 21% reduction in beta cell numbers within the islet compared with healthy non-diabetic mice (6726+/−450/mm$^2$ islet area vs 5289+/−387/mm$^2$, p=0.04). In comparison to streptozotocin-treated animals who received control, intra-arterial injection of STRO-1+ cells increased beta cell numbers by a mean of 8% (5709+/−690/mm$^2$), resulting in a mean reduction in beta cells compared with non-diabetic animals of only 15% (p=NS). In the fluorescent photomicrograph in Figure B, the beta cells within an islet of a representative non-diabetic control animal demonstrates the localization of typically densely packed insulin-positive fluorescent cells in the central area of the islet. However, in a representative STZ-treated mouse the beta cells are less abundant and display a disrupted pattern in the islet. The beta cells in a representative mouse treated with STRO-1+ cells demonstrate an intermediate pattern of fluorescence which is more abundant and less disrupted.

Figure 7C:
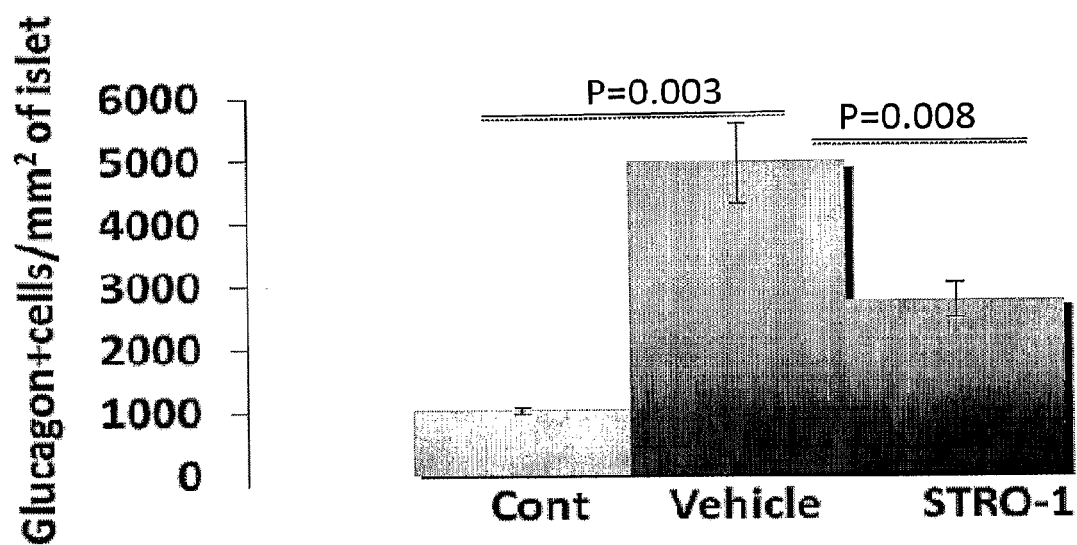
FIG. 7C is a graphical representation showing the effect of intra-arterial STRO-1⁺ cells on islet characteristics in STZ-induced diabetic NOD/scid mice after 21 days of cell therapy. Anti-glucagon stained pancreatic tissues were analyzed for glucagon positive cells per mm² of islet area. The data represents mean+/−sem; with vehicle group N=8, STRO-1 therapy N=6 and untreated controls (no STZ) N=3 animals. Student's T-Test was performed with significance at $p<0.05$.
Figure 7D:
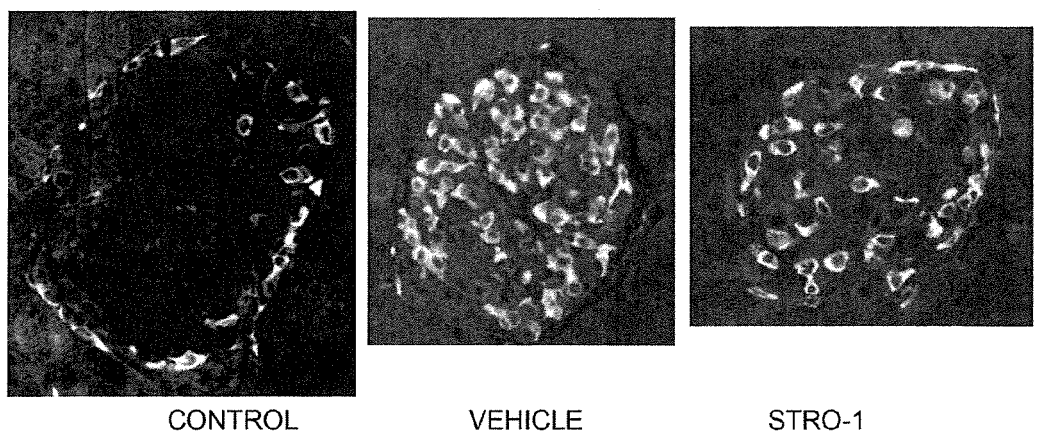
FIG. 7D is a copy of a series of micrographs (200×) showing antigen-retrieved formalin-fixed paraffin embedded sections that were stained with mouse anti-glucagon and detected with goat anti-mouse IgG-FITC conjugate. Treatment groups are indicated at the base of each photomicrograph.

Anti-glucagon mAb staining was used to quantify numbers of alpha cells within islets in pancreatic sections of healthy non-diabetic NOD/scid mice, diabetic NOD/scid mice treated with control media, and diabetic NOD/scid mice treated intra-arterially with STRO-1+ cells. As shown in FIG. 7C, streptozotocin treatment resulted in 470% increase in alpha cell numbers within an islet compared with healthy non-diabetic mice (1046+/−46/mm$^2$ islet area vs 4954+/−632/mm$^2$, p=0.003). In comparison to streptozotocin-treated animals who received control media, intra-arterial injection of STRO-1+ cells reduced alpha cell numbers by a mean of 44% (2764+/−274/mm$^2$, p=0.008), resulting in a mean increase in alpha cells compared with non-diabetic animals of only 164% (p=0.002). In the fluorescent photomicrograph shown in FIG. 7D, the alpha cells within the normal islet of a representative non-diabetic control animal can be identified as neat circumferentially arranged glucagon-stained cells. However, in a representative STZ-treated mouse the alpha cells are more abundant and display a diffuse pattern throughout the islet. The alpha cells in the islet of a representative mouse treated with STRO-1+ cells demonstrate a more peripheral pattern of fluorescence and are less abundant throughout the center of the islet.

Figure 7E:
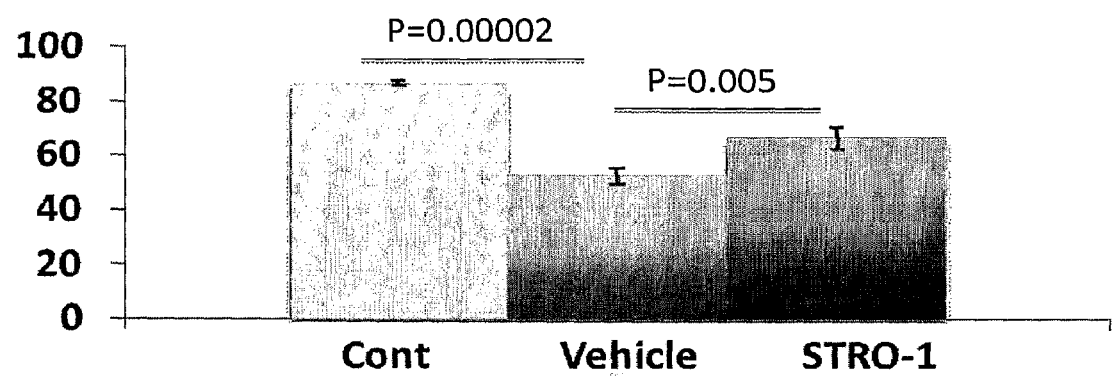
FIG. 7E is a graphical representation showing the number of intra-islet beta cells as a proportion of total alpha+beta cells. The data displayed was calculated from the numbers of insulin-positive cells/mm² of islet area and the numbers of glucagon-positive cells/mm² of islet area. The data represents mean+/−sem; with vehicle group N=8, STRO-1 therapy N=6 and untreated controls (no STZ) N=3 animals. Student's T-Test was performed with significance at $p<0.05$.

FIG. 7E depicts the proportion of beta cells relative to alpha cells within islets of pancreatic sections from healthy non-diabetic NOD/scid mice, diabetic NOD/scid mice treated with control media, and diabetic NOD/scid mice treated intra-arterially STRO-1+ cells. Streptozotocin treatment resulted in a 40% decrease in the percentage of beta cell numbers relative to total alpha and beta cells within an islet compared with healthy non-diabetic mice (86+/−0.9% vs 52+/−2.6%, p=0.00002). In comparison to streptozotocin-treated animals who received control media, intra-arterial injection of STRO-1¹ cells increased beta cell proportion relative to alpha cells by a mean of 29% (52+/−2.6% vs 67+/−3.9%, p=0.005). Thus, STRO-1+ cell treatment of NOD/scid mice rendered diabetic by streptozotocin resulted in a re-establishment of a more normal ratio of beta cells to alpha cells within the pancreatic islets.

Discussion

This study provides evidence for the first time that a single dose of human STRO-1¹ cells was effective for inducing sustained beta cell regeneration and reversing hyperglycaemia in NOD/scid mice rendered diabetic by streptozotocin. The streptozotocin (STZ)-induced experimental model of diabetes results in a diabetic phenotype similar to that seen following PDX-1 gene knockdown, with reduced numbers of insulin-producing beta cells, increased glucagon-producing alpha cells, and reduction in GLUT2 mRNA and protein expression (Liu et al., Mol Ther 15:86-93, 2007; and Wang et al., Diabetes 47:50-6, 1998). A single dose of STRO-1+ cells resulted in sustained PDX-1 activation, increased endogenous beta cell numbers, reduction in glucagon-expressing alpha cells, and enhanced insulin production.

Sustained induction in PDX-1 expression and re-established homeostasis between pancreatic beta and alpha cells in STZ-treated NOD/scid diabetic mice following a single dose of STRO-1+ cells are features strikingly similar to those reported following administration of gene therapy to induce long-term overexpression of glucagon-like peptide-1 (GLP-1) in the same murine model (Liu et al., Mol Ther 15:86-93, 2007). GLP-1 is a gut-derived peptide which migrates to the pancreas, activates PDX-1 and GLUT2, and results in increased insulin secretion. Its discovery has led to development of two new classes of agents which result in increased GLP-1 activity in beta cells: (a) GLP-1 analogs which are either long-acting receptor agonists or resistant to degradation by the natural antagonist of GLP-1, dipeptidyl peptidase IV (DPPIV), and (2) orally-active DPPIV antagonists which result in increased endogenous GLP-1 activity.

However, clinical use of these agents has been limited to the treatment of mild forms of type II diabetes. Their relatively short half-life, need for frequent administration, and relative lack of potency in cases of severe beta cell loss have precluded their use as insulin-sparing agents for type 1 diabetics or other insulin-dependent patients. Indeed, DPPIV antagonists are unable to reverse established diabetes in STZ-treated mice despite increasing endogenous GLP-1 levels (Kim et al., Diabetes 50:1562-1570, 2001), and are only able to improve hyperglycemia in the setting of sustained administration concomitant with low-dose STZ and partial beta cell loss (Mu et al., Diabetes 55:1695-1704, 2006). Similarly, GLP-1 agonists are only effective when given prior to or concomitantly with STZ and require sustained administration (Tourrell et al., *Diabetes* 50:1562-1570, 2001; Li et al., *J Biol Chem* 278:471-478, 2003; Gezginci-Oktayoglu and Bolkent, *Biochem Cell Biol* 87:641-651, 2009). Together, these data suggest that DPPIV inhibitors and GLP-1 analogs are only effective for facilitating beta cell regeneration when significant beta cell mass still exists.

In contrast, the present study suggests that even a single injection of STRO-1¹ cells can induce sustained beta cell regeneration even when little beta cell mass still exists. This is evidenced by the ability of the cells to reverse established hyperglycemia when administered 5 days after completion of a course of high-dose STZ, a model of complete beta cell loss. Similar outcomes can only be achieved by sustained overexpression of GLP-1 using gene therapy (Liu et al., *Mol Ther* 15:86-93, 2007). The long-lasting and potent effects of STRO-1$^+$ therapy indicate that this type of cell therapy may provide the sustained glucose control and insulin-sparing effects in insulin-dependent diabetics that DPPIV inhibitors or GLP-1 analogs cannot.

The invention claimed is:

1. A method for treating diabetic renal failure or syndrome X in a subject in need thereof, the method comprising administering to the subject STRO-1$^+$ cells and/or progeny cells thereof and/or soluble factors derived therefrom.

2. The method of claim 1, wherein the STRO-1$^+$ cells and/or progeny cells thereof and/or soluble factors derived therefrom are administered directly into the bloodstream of a subject.

3. The method of claim 2, wherein the STRO-1$^+$ cells and/or progeny cells thereof and/or soluble factors derived therefrom are administered intra-arterially.

4. The method of claim 1, wherein the STRO-1$^+$ cells administered to the subject are STRO-1$^{bri}$, and/or express tissue non-specific alkaline phosphatase (TNAP) and/or the progeny cells and/or soluble factors are derived from STRO-1$^+$ cells that are STRO-1$^{bri}$ and/or express TNAP.

5. The method of claim 1 for treating or delaying the progression of diabetic renal failure or syndrome X, wherein the STRO-1$^+$ cells and/or progeny cells thereof and/or soluble factors derived therefrom are administered following diagnosis of the diabetic renal failure or syndrome X.

6. The method of claim 1 additionally comprising monitoring or detecting onset and/or progression of diabetic renal failure or syndrome X.

7. The method of claim 1, wherein the STRO-1$^+$ cells and/or progeny cells thereof and/or soluble factors derived therefrom are administered in the form of a composition comprising said STRO-1$^+$ cells and/or progeny cells thereof and/or soluble factors derived therefrom and a carrier and/or excipient.

8. The method of claim 1, wherein the STRO-1$^+$ cells are culture expanded prior to administration to the subject.

* * * * *